United States Patent
Fourie et al.

(10) Patent No.: US 7,027,957 B2
(45) Date of Patent: Apr. 11, 2006

(54) CURRENT INTERRUPTER ASSEMBLY

(75) Inventors: Julius W. Fourie, Houston, TX (US);
Johan Oosthuysen, Gauteng (ZA)

(73) Assignee: American Innovations, Ltd., Austin, TX (US)

( * ) Notice: Subject to any disclaimer, the term of this patent is extended or adjusted under 35 U.S.C. 154(b) by 88 days.

(21) Appl. No.: 10/269,632

(22) Filed: Oct. 11, 2002

(65) Prior Publication Data

US 2003/0074162 A1 Apr. 17, 2003

Related U.S. Application Data

(60) Provisional application No. 60/348,845, filed on Jan. 15, 2002, provisional application No. 60/329,022, filed on Oct. 12, 2001.

(51) Int. Cl.
*G06F 15/00* (2006.01)

(52) U.S. Cl. ..................... 702/188; 324/424

(58) Field of Classification Search .............. 702/57, 702/60, 61, 64, 89, 104, 119, 177, 178, 184, 702/188; 324/72, 72.5, 330, 347, 348, 415, 324/700; 205/775.5; 204/196.03, 196.06; 73/40.5 R; 340/517, 645, 856.3, 664; 218/154; 335/6, 13

See application file for complete search history.

(56) References Cited

U.S. PATENT DOCUMENTS

| | | | | |
|---|---|---|---|---|
| 3,598,939 A | * | 8/1971 | Heberlein et al. | 200/48 R |
| 3,725,619 A | * | 4/1973 | McKinnon | 200/48 A |
| 3,828,307 A | * | 8/1974 | Hungerford | 340/909 |
| 3,860,912 A | * | 1/1975 | Romans | 340/870.18 |
| 4,031,346 A | * | 6/1977 | Bridges | 218/12 |
| 4,038,168 A | * | 7/1977 | Higuchi et al. | 204/196.15 |
| 4,061,965 A | * | 12/1977 | Nelson | 205/730 |
| 4,149,054 A | * | 4/1979 | Kopplin | 200/318 |
| 4,151,458 A | * | 4/1979 | Seager | 324/357 |
| 4,172,379 A | | 10/1979 | Van Tilburg et al. | 73/40.5 |
| 4,200,826 A | | 4/1980 | Calusio | 318/484 |
| 4,219,807 A | * | 8/1980 | Speck et al. | 340/664 |
| 4,220,951 A | * | 9/1980 | Bash et al. | 340/649 |
| 4,356,444 A | * | 10/1982 | Saenz, Jr. | 324/559 |
| 4,400,782 A | * | 8/1983 | Ishikawa et al. | 702/38 |
| 4,443,783 A | * | 4/1984 | Mitchell | 340/906 |

(Continued)

OTHER PUBLICATIONS

PCT Written Opinion for PCT Application No. PCT/US02/32532 dated Oct. 23, 2003 (5 p.).

(Continued)

*Primary Examiner*—Marc S. Hoff
*Assistant Examiner*—Mohamed Charioui
(74) *Attorney, Agent, or Firm*—Baker Botts L.L.P.

(57) ABSTRACT

A method for determining the influence of one of a plurality of cathodic protection circuits along a pipeline includes switching one of a plurality of cathodic protection circuits off, while the remainder of the plurality of cathodic protection circuits are left on, with a portable pipe-to-soil potential measurement unit measuring the pipe-to-soil potential along the pipeline. From these measurements, a calibration curve is generated and an apparatus for monitoring the cathodic protection circuits is strategically positioned on the pipeline. The apparatus includes a remote monitoring unit having a pipe-to-soil potential measurement unit for measuring the potential between the ground bed and pipeline. The remote monitoring unit is off except while making measurements. The remote monitoring unit may optionally include a pipeline current measurement unit connected at a second connection point on the pipeline for measuring the current passing through the pipeline between the first and second connection points.

6 Claims, 14 Drawing Sheets

U.S. PATENT DOCUMENTS

| | | | |
|---|---|---|---|
| 4,452,087 A * | 6/1984 | D'Antonio | 73/786 |
| 4,644,285 A | 2/1987 | Britton | 205/726 |
| 4,691,180 A * | 9/1987 | Grunert et al. | 335/6 |
| 4,775,865 A * | 10/1988 | Smith et al. | 340/906 |
| 4,823,072 A * | 4/1989 | Walcott et al. | 205/729 |
| 4,853,629 A * | 8/1989 | Rops | 324/207.2 |
| 4,857,921 A * | 8/1989 | McBride et al. | 340/912 |
| 4,888,706 A * | 12/1989 | Rush et al. | 700/283 |
| 4,945,775 A * | 8/1990 | Adams et al. | 73/865.8 |
| 5,139,634 A * | 8/1992 | Carpenter et al. | 205/727 |
| 5,300,905 A * | 4/1994 | Kolbas et al. | 335/167 |
| 5,325,047 A * | 6/1994 | Kempton | 324/72 |
| 5,331,286 A * | 7/1994 | Rivola et al. | 324/718 |
| 5,469,048 A * | 11/1995 | Donohue | 324/71.1 |
| H1644 H * | 5/1997 | Muehl, Sr. | 204/196.05 |
| 5,689,258 A * | 11/1997 | Nakamura et al. | 341/136 |
| 5,785,842 A * | 7/1998 | Speck | 205/777.5 |
| 5,999,107 A * | 12/1999 | Cooper et al. | 340/870.16 |
| 6,038,165 A * | 3/2000 | Miwa et al. | 365/185.03 |
| 6,107,811 A * | 8/2000 | Caudill et al. | 324/713 |
| 6,170,344 B1 * | 1/2001 | Ignagni | 73/865.8 |
| 6,243,657 B1 * | 6/2001 | Tuck et al. | 702/150 |
| 6,264,401 B1 | 7/2001 | Langner et al. | 405/169 |
| 6,469,918 B1 * | 10/2002 | Abramski | 363/45 |
| 6,479,780 B1 * | 11/2002 | Virtanen et al. | 218/154 |
| 6,492,898 B1 * | 12/2002 | Sabbattini et al. | 340/310.01 |
| 6,496,751 B1 | 12/2002 | Salvo et al. | 700/196 |
| 6,868,040 B1 * | 3/2005 | Vinegar et al. | 367/82 |
| 2001/0047247 A1 * | 11/2001 | Flatt et al. | 702/64 |

OTHER PUBLICATIONS

PCT International Search Report for PCT Appln. No. PCT/US02/32532 dated May 16, 2003 (5 p.).

* cited by examiner

CURRENT INTERRUPTER ASSEMBLY

CROSS-REFERENCE TO RELATED APPLICATIONS

This application claims the benefit of U.S. Provisional Patent Application Ser. No. 60/329,022 filed Oct. 12, 2001, and U.S. Provisional Patent Application Ser. No. 60/348,845 filed Jan. 15, 2002, which are both hereby incorporated herein by reference in their entirety.

STATEMENT REGARDING FEDERALLY SPONSORED RESEARCH OR DEVELOPMENT

Not Applicable.

FIELD OF THE INVENTION

The present invention relates generally to a method and apparatus for remotely monitoring cathodic protection and more particularly to an apparatus for remotely monitoring cathodic protection of a pipeline. Still more particularly, the present invention relates to a remote monitoring assembly, resistant to power surges, that may be located at preferred remote locations along the pipeline and communicate cathodic protection operations to a central location.

BACKGROUND OF THE INVENTION

It is known that all metallic structures that come in contact with a medium having the properties of an electrolyte are susceptible to the phenomenon of corrosion. Such corrosion tends to destroy the metallic structure and, depending upon the particular corrosive conditions existing, destruction of the metallic structure may occur within a longer or shorter period of time. In many instances significant damage to the metallic structure may occur within a short period of time even though destruction of the metallic structure has not yet occurred. There are many structures subject to corrosion damage, including bridges, pipes, storage tanks, reinforcing steel of concrete structures, structural steel and piles. In most cases the electrolytes for such structures comprise water with dissolved salts and moist soils.

In order to prevent/minimize corrosion, cathodic protection systems (CPSs) are often employed. CPS design is influenced by numerous factors, including the type of metal to be protected, properties of the electrolyte (chemical, physical and electrical), temperatures, presence or absence of bacteria, shape of the structure, design life, constructability and maintainability. Cathodic protection (CP) is often applied to coated structures, with the coating providing a primary form of protection and an electric current providing a secondary protection.

In general, CPSs operate by utilizing an electrical current to oppose a corrosion current between the structure being protected and an electrolyte. There are basically two known systems for generating opposing electrical currents, "sacrificial systems" and "impressed current systems." In sacrificial systems, the current is supplied by another metal which is galvanically more reactive than the metal of the structure. For example, metals such as aluminum, magnesium and zinc are galvanically more active than steel and are used as "sacrificial anodes" to protect steel structures. In impressed current systems, a consumable metal is used to drain direct current (DC) supplied from an external source into the electrolyte, which passes to the structure to be protected. The parts from which the current is drained are called "anodes" and the protected structure is called a "cathode". In both sacrificial and impressed current systems of cathodic protection, a metallic path between the anode and the cathode is essential for flow of current to protect the structure.

As stated above, in impressed current cathodic protection, a DC current is applied to a buried structure and flows onto the structure at coating defects. The applied current changes the voltage across the metal/soil interface. This change in voltage changes the electrochemical state of the structure to the extent that corrosion ceases.

The voltage across the metal/soil interface can be measured by monitoring the voltage difference between the structure and a second dissimilar metal (reference electrode) in contact with the soil. By monitoring the voltage difference it can therefore be determined if corrosion protection of the structure is being achieved. The cathodic protection circuits may be monitored at "test stations," e.g., wire connections to the buried structure that terminate in some way above ground. If the structure is a pipeline, test stations are installed at regular intervals on a pipeline (typically one-mile apart) and often at road crossings for accessibility. A portable pipe-to-soil measurement unit is used to measure the voltage difference between the pipeline and the reference electrode at each test station by having an individual visit each test station along the pipeline and take manual measurements at each test station. The measured voltage level is termed a "pipe-to-soil" potential.

The pipe-to-soil potential measurement unit includes a volt meter having a test lead extending from the volt meter to the wire connection extending from the pipeline. The pipe-to-soil potential measurement unit also includes a reference electrode in contact with the ground above the buried pipeline. The reference electrode has an electrode potential that does not vary such that it supplies the pipe-to-soil potential measurement unit with a stable reference potential. The reference electrode typically includes a copper rod in a copper sulfate solution. The volt meter then measures the potential difference between these two half-cells and the value of this potential difference is the pipe-to-soil potential. The pipe-to-soil potential will vary depending upon the current that is being supplied to the pipeline by virtue of one or more of the cathodic protection systems along a particular length of the pipeline.

A cross-country pipeline will have numerous cathodic protection circuits with power source installations, or rectifiers, on each circuit to distribute the impressed current along the entire length of the pipeline. The spacing between cathodic protection circuits depends on many factors including soil conditions and coating quality, but typical spacing is approximately 10 to 30 miles apart.

Typically if there is no current being supplied to the pipeline by cathodic protection circuits, the pipe-to-soil potential is approximately −0.5 to −0.6 volts. This is referred to as the "static" or "native" potential. The "static" or "native" potential may be measured after the cathodic protection circuits have been off for such a period of time that the current from the cathodic protection circuits no longer influences the pipe-to-soil potential. As current is supplied to the pipeline by the cathodic protection circuits, the pipe-to-soil potential will tend toward the negative, preventing corrosion from forming. This is referred to as the "on" potential. Various criteria are used in the industry to determine if the pipe-to-soil potential has been shifted sufficiently negative to prevent corrosion. The most common criterion is that the potential difference, while the cathodic protection circuits are switched on, is more negative than −0.85V.

Each cathodic protection circuit with a rectifier will have an influence along a particular length of the pipeline, i.e., an area of influence. The current difference between a particular cathodic protection circuit being on or off determines the influence of that cathodic protection circuit on the pipe-to-soil potential at any particular point along the pipeline. When a cathodic protection circuit is turned off, there is a drop in current flow to the pipeline causing an increase in the pipe-to-soil potential measured by the pipe-to-soil measurement unit. This change in pipe-to-soil potential or influence of a particular rectifier can be measured with a portable pipe-to-soil measurement unit at each test station by measuring the pipe-to-soil potential with a rectifier switched on and measuring it with the rectifier switched off. The difference between these two values is the influence that the switched on rectifier has on the pipe-to-soil potential. The influence will depend upon the size of the rectifier and how much power it is sending into the soil as well as the local soil condition for current flow. The condition of the coating on the pipeline is also a factor.

By measuring the influence of each rectifier at each test station, it is therefore possible to obtain a profile of the influence of each rectifier along the pipeline. The information obtained from measuring the influence of individual rectifiers is used for specialized troubleshooting of cathodic protection systems and it is not typically used as a routine monitoring procedure.

Routine monitoring of cathodic protection systems is important to ensure that the protected structure remains in good condition. Basic routine monitoring of CPSs determines the measured status of the CPSs and includes 1) checking that all rectifiers are functioning and supplying current to the structure and 2) checking that the pipe-to-soil potential with all the rectifiers in the "on" position, is maintained at a value more negative than −0.85V using a copper/copper sulfate reference electrode at all test stations along the length of the structure. If, when using a copper/copper sulfate reference electrode, the pipe-to-soil potential is more negative than −0.85V, the steel pipeline is receiving corrosion protection.

Instead of physically visiting rectifiers to check that they are functioning and supplying current to the structure, devices known as "remote monitoring units" or RMUs may be used to remotely monitor the rectifiers from a central location. These devices use some form of communication method to automatically transmit the measured status of a rectifier to a central location. A typical remote monitoring device for rectifiers using Low Earth Orbital (LEO) satellites as the communication link is described in U.S. Pat. No. 5,785,842.

Typically, RMUs are installed inside each rectifier of a cathodic protection circuit. This allows the RMU to remotely read the status of the rectifier and the pipe-to-soil potential at the rectifier. The most common problem associated with the remote monitoring devices is failures that occur as a result of electrical surges, either from the alternating current (AC) supply within the rectifier or through the connection to the pipeline or the connection to the anodes. The remote monitoring described above also has the disadvantage that information on the cathodic protection (CP) status at the rectifier is limited; because the rectifier is the point source of current being supplied to the pipeline, and therefore the pipe-to-soil potential at that point will invariably be satisfactory. Pipe-to-soil potentials of −2V to −3V are very typical. As a result, the CP engineer has to rely on manual pipe-to-soil readings at test stations to ensure that a good CP profile exists along the pipeline.

Because cathodic protection remote monitoring devices installed in rectifiers do not monitor the pipe-to-soil potential along the pipeline, manual testing to determine the pipe-to-soil potentials along the pipeline is necessary in addition to monitoring the rectifier itself to ensure proper functioning of CPSs. Typically, manual pipe-to-soil potential data at test stations is limited to monthly or annual evaluations, so CPSs may be incorrectly preventing corrosion for some period of time before damage is detected. Furthermore, remote monitoring devices are susceptible to failure caused by electrical surges, thereby decreasing the usefulness of these devices to monitor the proper functioning of the rectifiers. Manual testing of pipe-to-soil potentials along the pipeline and repairing remote monitoring units damaged by electrical surges is expensive, time-consuming and produces dated information. Despite the known deficiencies possessed by current RMUs, to date no one has developed an arrangement that correctly obtains information about the pipe-to-soil potential along the pipeline, while simultaneously determining the status of rectifiers and also preventing failure from electrical surges. More specifically, to date no one has developed a remote monitoring arrangement that utilizes rectifier influence data to determine the status of rectifiers.

One way of protecting components susceptible to damage by electrical surges is to electrically disconnect the components from the source of the surge during times when the device is not used. A normal switch (e.g. a relay) may not be sufficient because if the surge is big enough, it will jump across the air gap or arcing will occur between one contact and the relay circuitry. A disconnect device has been described in U.S. Pat. No. 5,453,899 that senses the presence of an electrical storm and then unplugs the electrical apparatus from the AC power if an electrical storm is detected. In this case, arcing is avoided by placing a dielectric material between the contact points after the apparatus is disconnected.

In order to determine the influence from individual rectifiers, it is necessary to (1) switch each of the rectifiers off and measure the pipe-to-soil potential at each test station and then (2) switch each of the rectifiers back on and measure the pipe-to-soil potential at each test station. The shift of the pipe-to-soil potential from off to on for each individual rectifier can then be determined at each test station. Instead of manually switching each rectifier off and on, it is common in the CP industry to install a current interrupter into the rectifier under investigation. By installing an interrupter into a rectifier, it is therefore possible to visit each of the test stations and measure the influence of the rectifier being interrupted. A current interrupter is a device that interrupts the output from the rectifier in a periodic fashion and it is typically programmable so that the length of the on and off cycles can be adjusted. The influence of other rectifiers is then measured by moving the interrupter to each of these rectifiers in turn and re-visiting each of the test stations. This cycle is repeated for each cathodic protection circuit influencing that length of the pipeline. Thus if there are four cathodic protection circuits affecting a particular length of the pipeline, this cycle will need to be performed four times until the influence of each one of the rectifiers at the cathodic protection circuits has been measured at each of the test stations along the length of the pipeline.

Current interrupters are also used to determine "instant off" pipe-to-soil potentials at test stations. If a pipe-to-soil potential is measured with rectifiers switched on, there is an inherent error in the measured value because of a voltage drop that occurs due to current flow through the soil. To minimize the effect of rectifier current, the rectifiers are turned off and the pipe-to-soil potential is immediately measured using the voltmeter (typically within 1 second). This value is referred to as the "interrupted off" or "instant off" potential. By measuring at "instant off," any error introduced due to the current of the rectifiers is minimized. This is achieved by installing current interrupters into each influencing rectifier and programming these interrupters to switch off and on at the same time. The interrupters generate "on" and "off" cycles for all of the influencing rectifiers. Some of the available interrupters only have fixed "on" and "off" cycles, while others are programmable and the length of the "off" and of the "on" cycle can be adjusted. Some models also have the ability to program a start and stop time for the interruption cycle. In all the equipment currently available, all of the interrupters switch on and off at the same time. Synchronization of the various interrupters is achieved through synchronizing their internal clocks, often using satellite time signals. U.S. Pat. No. 4,356,444 describes a plurality of interrupters which switch rectifiers on and off in unison. Each interrupter is synchronized with a clock reference unit.

The testing to determine rectifier influence at each test station requires moving an interrupter from rectifier to rectifier and visiting each of the test stations once for each influencing rectifier. For example, if four rectifiers influence a specific length of pipeline, the interrupter will have to be moved four times and each of the test stations will have to be visited four times. If the "instant off" value also needs to be measured at each test station, it will be necessary to install interrupters into all four rectifiers in order to cycle the rectifiers on and off simultaneously. A fifth visit must then be made to each of the test stations to measure the "instant off" pipe-to-soil potential. Currently no device is available that will allow measurement of the influence from each rectifier and the "instant off" pipe-to-soil potential without having to go through each measurement sequence described above.

In addition to measuring "instant off" pipe-to-soil potential at each test station (typically spaced 1 mile apart), sometimes it is desirable to measure "instant off" pipe-to-soil potentials at regular intervals between test stations using a methodology known as a close interval survey (CIS). A CIS is performed when the data collected at test stations alone is deemed inadequate and a higher density of data points is required. A CIS is typically performed on a pipeline using a portable pipe-to-soil measurement unit connected to a test station with the reference electrode on the portable pipe-to-soil measurement unit being manually inserted into the ground at spaced intervals between adjacent test stations and a pipe-to-soil measurement taken at each interval. The spacing of data collection points on a CIS varies, but 2.5 to 5 foot intervals are typical. At present, there is also no way of obtaining the rectifier influence in conjunction with a CIS because during a CIS, the interrupters are programmed to simultaneously switch all the rectifiers either all on or all off.

The present invention overcomes the deficiencies of the prior art.

SUMMARY OF THE INVENTION

The present invention relates to a cathodic protection remote monitoring unit and method. The remote monitoring unit includes a pipe-to-soil potential measurement unit installed at a test station where the influence of at least one rectifier on the pipe-to-soil potential is known. The pipe-to-soil measurement unit is connected to the pipeline at a first connection point for measuring the potential between a reference electrode and a pipeline at that location. The remote monitoring unit may optionally include a pipeline current measurement unit connected at a second connection point on the pipeline for measuring the current passing through the pipeline between the first and second connection points. The remote monitoring unit monitors the pipe-to-soil potential and by comparing changes in this measured value with the known influence of at least one rectifier, the status of at least one rectifier is monitored. If a pipeline current measurement unit is included, the remote monitoring unit also monitors the amount of current flowing between the first and second connection points. By comparing changes in this measured current value with the known effect that at least one rectifier has, the status of at least one rectifier is monitored.

In a preferred embodiment of a method of the present invention, a calibration curve is generated showing the influence of each of the cathodic protection circuits at each test station along the pipeline to strategically position each of the remote monitoring units along the pipeline. To determine the influence of each of the plurality of cathodic protection circuits along the pipeline, each one of a plurality of cathodic protection circuits is turned off, while the remainder of the plurality of cathodic protection circuits are left on, with a portable pipe-to-soil potential measurement unit manually measuring the pipe-to-soil potential at each test station along the pipeline. This cycle is repeated until each of the plurality of cathodic protection circuits has been switched off and its influence on the pipe-to-soil potential on the pipeline has been determined. The calibration curve for each cathodic protection circuit is then generated from these measurements. From the calibration curves, a remote monitoring unit is strategically positioned on the pipeline at a location where the pipe-to-soil potential influence of each cathodic protection circuit at such location is distinct and discernable from the measurements taken by the remote monitoring unit at that location.

The remote monitoring unit is prone to damage by electrical surges. A switch is connected in the AC power and measuring circuits of the remote monitoring unit. The switch maintains the remote monitoring unit in the off position until a measurement is to be made. The switch has a disconnect position which separates the contacts between the remote monitoring unit and the AC power source and the measurement circuit a sufficient distance to prevent any electrical arc therebetween. The normally off position of the switch and the distance between the contacts on the switch prevent failure of the remote monitoring unit from electrical surges, thereby ensuring the successful operation and substantially increasing the lifetime of the remote monitoring units.

A method of measuring instant "off", rectifier influence, and "on" potential for first and second rectifiers in cathodic protection circuits includes: (a) measuring pipe-to-soil potential while the first and second rectifiers are off and recording the instant "off" potential; (b) measuring pipe-to-soil potential while the second rectifier is on and the first rectifier is off and recording the influence of the first rectifier; (c) measuring pipeline current influence while the first rectifier is on and the second rectifier is off and recording the influence of the second rectifier; and (d) measuring pipeline current influence while the first and second rectifiers are on and recording the "on" potential. Interrupters may be used to program the sequence of turning the rectifiers on and off.

Other objects and advantages of the invention will appear from the following description.

BRIEF DESCRIPTION OF THE FIGURES

A better understanding of the present invention can be obtained when the following detailed description of the preferred embodiment is considered in conjunction with the following drawings.

Figure 1:
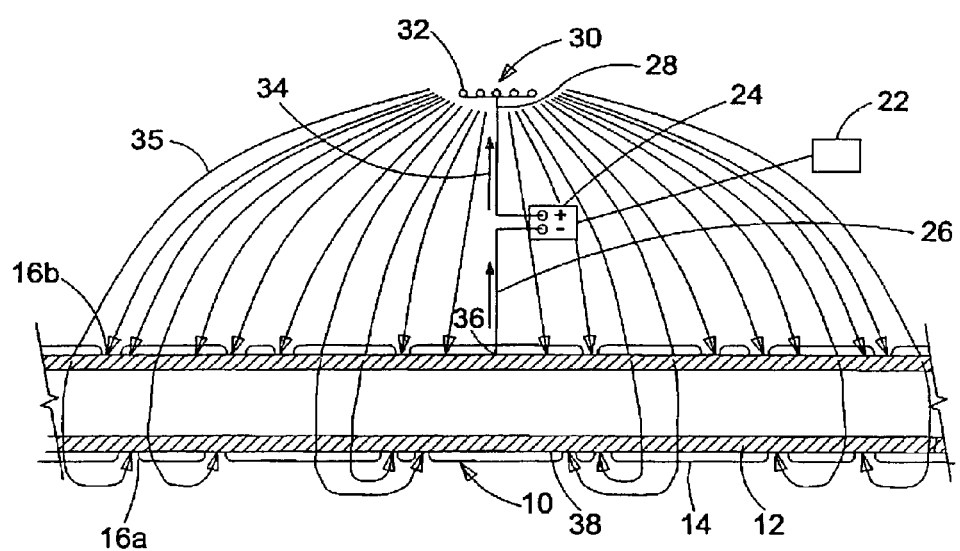
FIG. 1 is a schematic of a cathodic protection circuit.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

In the description which follows, like parts are marked throughout the specification and drawings with the same reference numerals, respectively. The drawing figures are not necessarily to scale. Certain features of the invention may be shown exaggerated in scale or in somewhat schematic form and some details of conventional elements may not be shown in the interest of clarity and conciseness.

The present invention relates to methods and apparatus for remotely monitoring cathodic protection. The method and apparatus is described for use in monitoring cathodic protection on a pipeline but it should be understood that the method and apparatus of the present invention is susceptible to embodiments of different forms and may be used for monitoring cathodic protection of any metal structure. There are shown in the drawings, and herein will be described in detail, specific embodiments of the present invention with the understanding that the present disclosure is to be considered an exemplification of the principles of the invention, and is not intended to limit the invention to that illustrated and described herein. For example, it will be understood that a remote monitoring unit measures pipe-to-soil potential, but may optionally measure other parameters such as current, etc. It is to be fully recognized that the different teachings of the embodiments discussed below may be employed separately or in any suitable combination to produce desired results. Additionally, certain terms may be used throughout the specification interchangeably. For example, the terms "pipe-to-soil potential" and "electrical potential" are synonymous.

Referring initially to FIG. 1, there is shown a pipeline 10 made up of pipes 12 for transporting fluids or gasses such as water or hydrocarbons, e.g., oil or gas. The pipeline is typically buried in the ground and has an organic coating 14 therearound to protect the pipeline 10 against corrosion. Typical organic type coatings include an asphalt or carbon based coating, fusion bonded epoxies, plastic wrap or the like.

Figure 2:
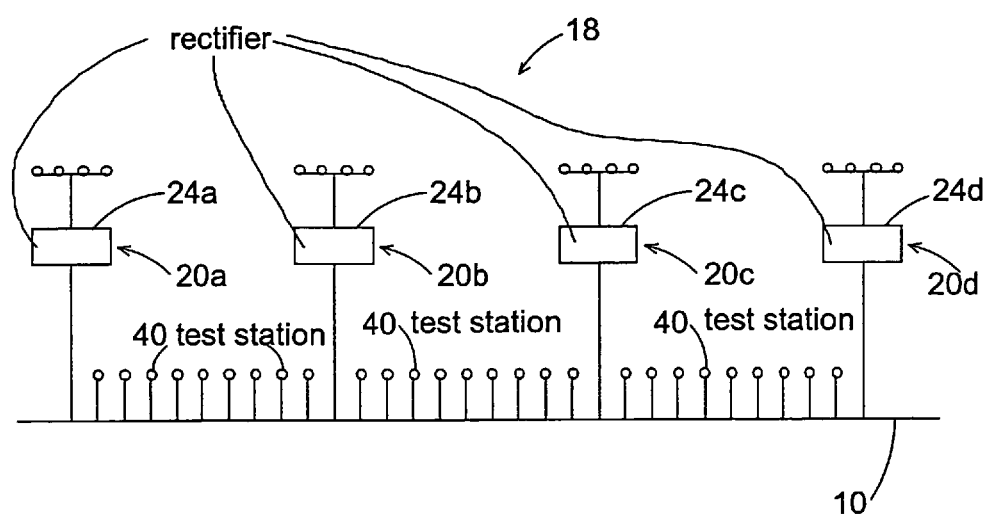
FIG. 2 is a schematic of a cathodic protection system.

Referring now to FIGS. 1 and 2, there is shown in FIG. 2 a cathodic protection system 18 including a plurality of the cathodic protection circuits 20 shown in FIG. 1. Over time, the coating material 14 may develop defects 16, such as cracks or breaks 16a,b. To prevent corrosion at these defects 16, cathodic protection system 18 is disposed on pipeline 10.

Referring particularly to FIG. 1, each cathodic protection circuit 20 includes a power source 22, such as an overhead power line, providing alternating current to a rectifier 24. The rectifier 24 transforms the alternating current from power source 22 to direct current for use in the cathodic protection circuit 20. Cathodic protection circuit 20 includes a first electrical conduit 26 extending to the pipeline 10 and a second electrical conductor 28 extending to a ground bed 30. The electrical conductor 26 has one end 36 welded to the surface 38 of a pipe 12 of pipeline 10 with the connection then being coated with a coating material for corrosion protection. Ground bed 30 includes a plurality of buried conductors 32 serving as anodes for passing current 34 into the soil.

In operation, current 34 flows from the power source 22 to the rectifier 24 and then to ground bed 30. The current 34 then flows through the soil as indicated by arrows 35 to the pipeline 10. Current 34 from the pipeline 10 then flows back to the rectifier 24 via steel pipes 12 and electrical conductor 26. The current 34 passing onto the steel pipes 12 at defects 16 changes the electrochemical characteristic potential of the surface 38 of the pipes 12 of pipeline 10 so as to inhibit corrosion. The corrosion protecting coating material 14 is the primary form of corrosion protection for the pipeline 10, while the cathodic protection provided by cathodic protection system 18 is the secondary form of corrosion protection.

The number of cathodic protection circuits 20 in system 18 depends upon the condition of the coating material 14 on the surface 38 of the pipeline 10 and the condition of the soil for conducting current 34. If the coating material 14 is in poor condition or the soil condition is unfavorable for conducting current 34, then a greater number of cathodic protection circuits 20 will be required by pipeline 10. If the pipeline 10 is bare, having no coating around it, the greatest number of cathodic protection circuits 20 will be required by pipeline 10.

Regulations require that the pipeline 10 be inspected regularly, such as at least once every one to three months, to ensure that each cathodic protection circuit 20 is operating and in a good condition. Each rectifier 24 includes a device that permits a determination as to whether rectifier 24 is on and to ensure that current 34 is flowing, such as providing 10 amps and 12 volts of current output. This device may allow remote monitoring of the rectifiers 24 so as to send the results to a central location on a daily or weekly basis by some remote transmission method. Further, typically once a year, it is necessary that the electrical potential is measured along the pipeline 10 to ensure that the cathodic protection is working and that the coating 14 on the pipeline 10 is not deteriorating.

In the prior art, an inspector manually makes an inspection of each rectifier 24 to ensure that the rectifiers 24 are receiving AC power, that they are providing a DC output, and that the rectifiers 24 are in good operating condition. The frequency of these rectifier 24 inspections is typically once per month. Sometimes, a remote monitoring device is installed into the rectifier and the output current and output voltage of the rectifier is transmitted periodically to a central location, in which case visits to the rectifier to manually check the output are no longer required. Furthermore, the inspector typically manually performs an inspection of each test station 40 to ensure that the output from the rectifiers 24 are resulting in a satisfactory pipe-to-soil potential at each test station 40. These test station 40 inspections are typically carried out once per year using a portable pipe-to-soil measurement unit.

Figure 3:
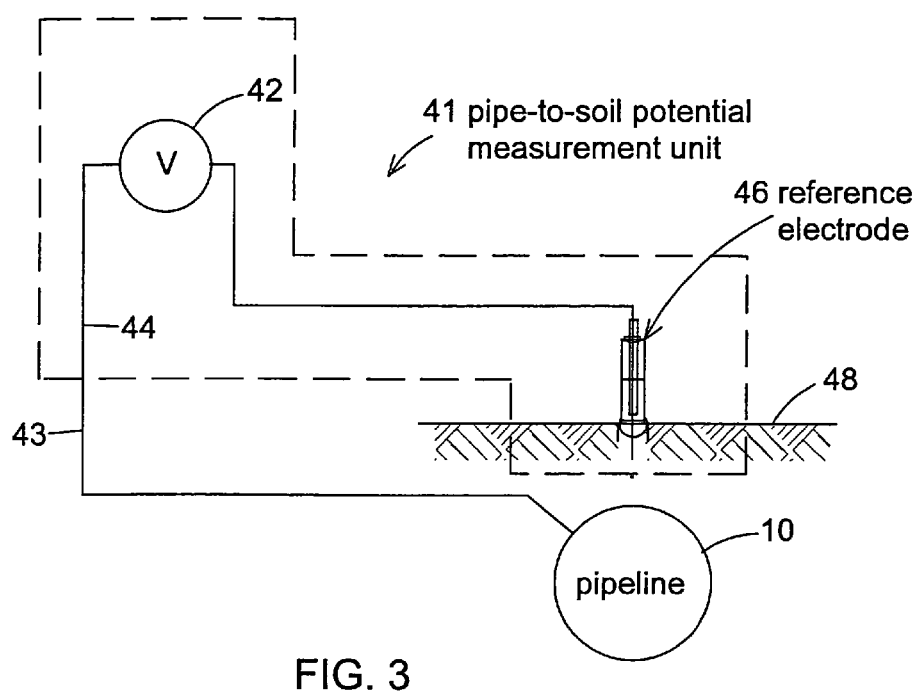
FIG. 3 is a schematic of a pipe-to-soil measurement unit.

Referring now to FIG. 3, there is shown a pipe-to-soil potential measurement unit 41 for measuring the effect of the current 34, being supplied by a cathodic protection circuit 20 on the pipeline 10 at one of the test stations 40. The pipe-to-soil measurement unit 41 is normally portable but may also be installed at the pipeline such as in a remote monitoring unit, hereinafter described. The pipe-to-soil potential measurement unit 41 includes a volt meter 42 having a test lead 44 extending from the volt meter 42 to a wire connection 43 extending to and connected with the surface 38 of pipeline 10. The pipe test lead 44 is electrically connected to wire connection 43 from the pipeline 10 above ground. The pipe-to-soil potential measurement unit 41 also includes a reference electrode 46 extending into the ground 48. The reference electrode 46 has an electrode potential that does not vary such that it supplies the pipe-to-soil potential measurement unit 41 with a stable reference potential. The reference electrode 46 typically includes a copper rod in a copper sulfate solution. Volt meter 42 then measures the potential difference between these two half-cells. The difference in potential will vary depending upon the current 34 that is being supplied to pipeline 10 by virtue of one or more of the cathodic protection systems 18 along the length of the pipeline 10.

To monitor the cathodic protection circuits 20, a pipe-to-soil measurement is carried out at each test station 40 using pipe-to-soil potential measurement unit 41. As current is supplied to the pipeline 10 by cathodic protection system 18, the pipe-to-soil potential measured by voltmeter 42 will tend toward the negative, preventing corrosion from forming. Various criteria are used in the industry to determine if the pipe-to-soil potential has been shifted sufficiently negative to negate or prevent corrosion. The most common criterion is that while the cathodic protection circuits 20 are switched "on", the potential difference measured by voltmeter 42 is more negative than −0.85V when using a copper/copper sulfate reference electrode. This is referred to as the "on" potential.

A second criterion includes the measurement of the pipe-to-soil potential by voltmeter 42 immediately (typically within 1 second) after switching the cathodic protection circuits 20 off. In this way, possible errors that may be inherent in measuring the pipe-to-soil potential while the cathodic protection circuits 20 are energized are eliminated. This value is the "instant off" potential. A third criterion requires that the difference between the "instant off" and the "static" potential is at least 0.1 V. The "static" or "native" potential is measured by voltmeter 42 and is approximately −0.5 volts to −0.6 volts.

For the purpose of the following discussion, the "on" potential will be used, unless where stated otherwise. It is understood that when using the "on" potential, all rectifiers are providing cathodic protection to pipeline 10, such that the potential difference measured by voltmeter 42 is more negative than −0.85V when using a copper/copper sulfate reference electrode.

Figure 4:
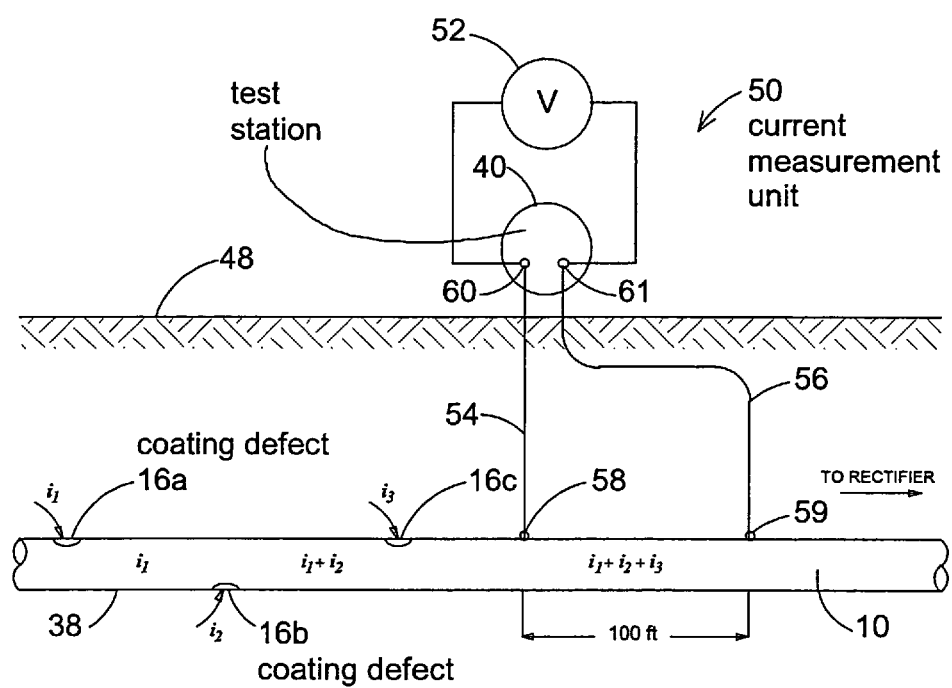
FIG. 4 is a schematic of a pipeline current measurement unit.

Referring now to FIG. 4, pipeline current measurement unit 50 may be used to measure the portion of current 34 flowing back to the rectifier in pipeline 10 at test station 40. Each coating defect 16a,b,c permits current $i_1$, $i_2$, $i_3$ to reach the surface 38 of the metal pipes 12 of pipeline 10 and send current $i_1$, $i_2$ and $i_3$ down the pipeline 10. For example, defect 16a allows a certain amount of current $i_1$ to enter the pipeline 10 while defects 16b and 16c add additional current flow $i_2$ and $i_3$ to the pipeline 10. Pipeline current measuring unit 50 includes a volt meter 52 connected to terminals 61, 62 inside test station 40. First electrical conduit 54 extends from terminal 60 and is attached to pipeline 10 at connection point 58. Second electrical conduit 56 extends from terminal 61 and is attached to the pipeline 10 at connection point 59. Connection points 58, 59 are some distance from each other so as to provide a span or distance between connection points 58, 59, such as 100 to 300 feet. The voltage drop between connection points 58, 59 is therefore measured between terminals 60, 61 and this voltage drop measures the portion of the total current 34 picked up by the section of pipeline 10 by virtue of the coating defects 16.

The pipeline current measurement unit 50 is one method of measuring the current flow back towards a rectifier 24 along the pipeline 10. Unit 50 measures the potential difference between connection points 58, 59, which are a distance apart, since a particular span along the pipeline 10 will provide a particular resistance to current flow. By measuring the voltage drop that occurs over that resistance, the current actually flowing at a particular point along the pipeline 10 can be measured assuming the resistance is known. The unit 50 determines what portion of current 34 is flowing back to a rectifier 24 at measurement point 58. For example, the resistance along a particular pipe span may be approximately 0.5 milliohm and the voltage drop across this pipe span may be 0.75 mV, such that the portion of current 34 flowing in the pipeline 10 at this particular measurement point may be approximately 1.5 amps. The amount of current flowing back to the rectifier at any given point will change if a rectifier output is changed or if it goes out of service. The pipeline current measurement unit 50 measures this additional parameter as compared to the pipe-to-soil potential measurement unit 41 at a test station 40.

Figure 5:
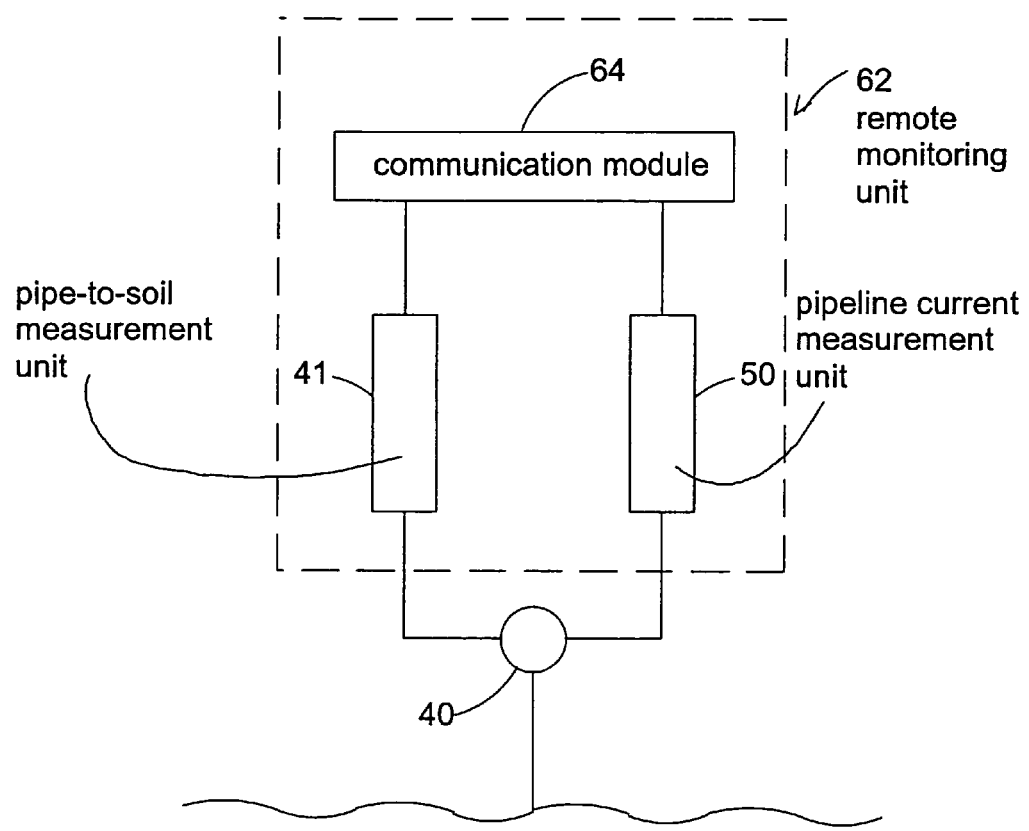
FIG. 5 is a remote monitoring unit incorporating a pipe-to-soil measurement unit and a pipeline current measurement unit.

Referring now to FIG. 5, there is shown a remote monitoring unit 62 installed at test station 40 which includes both a pipe-to-soil measurement unit 41 and a pipeline current measurement unit 50. Pipe-to-soil measurement unit 41 measures the pipe-to-soil potential and this value is transmitted via the communications module 64 to a central location. The remote monitoring unit 62 also includes pipeline current measurement unit 50 which measures the portion of current 34 flowing back to rectifier 24 through steel pipe 12 of pipeline 10 at test station 40 where remote monitoring unit 62 is installed. This value is also transmitted via communication module 64 to a central location. Remote monitoring unit 62 may include both pipe-to-soil measurement unit 41 and pipeline current measurement unit 50 or it may include either pipe-to-soil measurement unit 41 or pipeline current measurement unit 50 only. Thus, remote monitoring unit 62 may only measure and transmit a pipe-to-soil value or a pipeline current value only, or it may measure and transmit both of these values.

Referring again to FIG. 2, there is shown a typical impressed current cathodic protection system 18 with a plurality of test stations 40 disposed along the length of pipeline 10. Each of the test stations 40 is within the influence area of a cathodic protection circuit 20, such as circuits 20a,b,c,d, with the test stations 40 typically being 1 mile apart. Each of the rectifiers 24a,b,c,d for the cathodic protection circuits 20a,b,c,d supply current 34 to a portion or section of pipeline 10. The total amount of current being supplied to pipeline 10 by cathodic protection circuits 24a, b,c,d therefore determines the pipe-to-soil potential profile along pipeline 10 as measured at test stations 40 with all the cathodic protection circuits 24a,b,c,d on and in good operating condition. Any change in output from cathodic protection circuits 24a,b,c,d, such as one circuit going out of operation, will change the potential profile along pipeline 10. Each cathodic protection circuit 20 thus has an influence on the pipe-to-soil potential of pipeline 10. That influence can be measured at test stations 40 as a change in pipe-to-soil potential.

Figure 6:
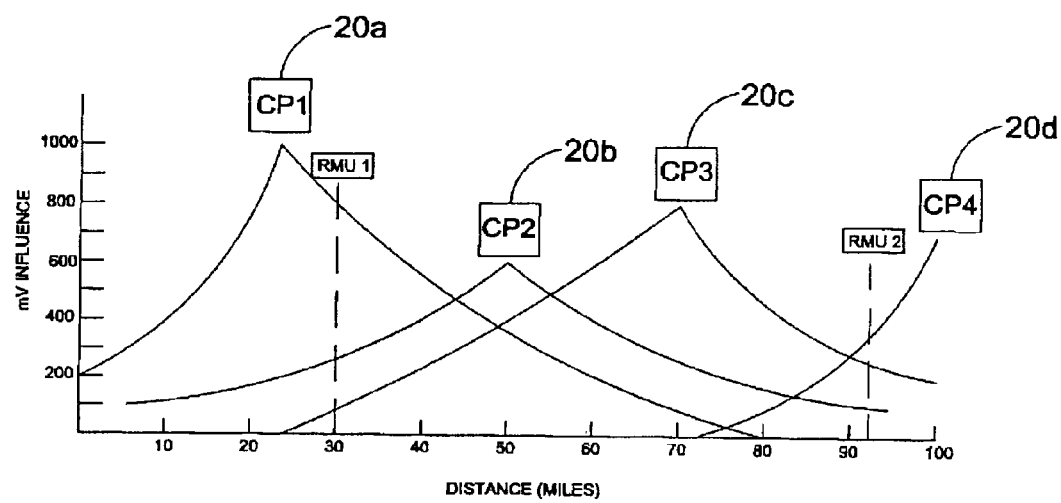
FIG. 6 is a calibration chart showing the influence on pipe-to soil potential value of four rectifiers along 100 miles of pipeline.

Referring now to FIG. 6, a voltage influence chart depicting the influence of a plurality of cathodic protection circuits $CP_1$, $CP_2$, $CP_3$, and $CP_4$ on a pipeline 10 is shown. The chart includes a graph plotting the data from conducting pipe-to-soil measurements while switching each of the plurality of cathodic protection circuits 20 along a length of the pipeline 10 off and back on again. The voltage influence curves of FIG. 6 are developed by switching one of the rectifiers 24 at cathodic protection circuits 20 off, while the others remain on, and measuring the pipe-to-soil potential at each test station 40 with a portable pipe-to-soil measurement unit 41. This cycle is repeated until each one of the rectifiers 24 at cathodic protection circuits 20 have been switched off and back on again, and the pipe-to-soil potential during this off and on event has been measured at each test station.

When any particular cathodic protection circuit 20 is turned off, there is a drop in current flow to the pipeline 10 causing an increase in the pipe-to-soil potential measured by pipe-to-soil measurement unit 41. The current difference between a particular cathodic protection circuit 20 being on or off determines the influence that cathodic protection circuit 20 has on the pipe-to-soil potential at that particular point along pipeline 10. The change in pipe-to-soil potential at every test station 40 resulting from cathodic protection circuit 20 being switched off and on again can be measured as a change in pipe-to-soil potential (voltage) at every test station 40 along pipeline 10. FIG. 6 shows this voltage change at every test station 40 as a voltage influence curve for each cathodic protection circuit 20 along pipeline 10.

In FIG. 6, because there are four cathodic protection circuits, this measurement procedure will need to be done four times. Each rectifier 24 will provide a different current signature along the pipeline 10. This is shown in FIG. 6 by each of the cathodic protection circuits 20 providing a different voltage influence along the pipeline. The four peaks shown in FIG. 6 correspond to the locations of the four cathodic protection circuits 20 along the pipeline 10. The influence will depend upon the size of the rectifier 24 and how much power it is sending into the soil as well as the local soil condition for current flow. The condition of the coating 14 and the corrosive nature of the soil around pipeline 10 are also factors.

Note that the cathodic protection circuits 20 need not be the same distance apart. In the example in FIG. 6, some are approximately 10 miles apart while others are 30 miles apart. Also, the voltage influence curves for each of the rectifiers 24 in the cathodic protection circuit 20 are not necessarily symmetrical.

Because each cathodic protection circuit 20 has a specific voltage influence curve along a length of pipeline 10 and because the voltage influence curves for cathodic protection circuits 20a,b,c,d overlap each other, it is possible to determine a position where a remote monitoring unit 62 incorporating a pipe-to-soil measurement unit 41, could monitor more than one cathodic protection circuit 20. By placing a remote monitoring unit 62 at a strategic position, it is therefore possible to "see" a cathodic protection circuit 20 switching off at the remote monitoring unit 62 placed remotely from the cathodic protection circuit 20, because the pipe-to-soil potential at the remote monitoring unit 62 will become more positive as soon as the cathodic protection circuit 20 is switched off. The location of the remote monitoring unit 62 is then made at a location where the influences of the different influencing cathodic protection circuits 20 is distinct and discernable, such as differing by more than 10 milli-volts between influencing rectifiers. This can be seen from the placement of the remote monitoring units RMU 1 and RMU 2 shown in FIG. 6 where there is a substantial difference in pipe-to-soil potential between the influencing rectifiers in $CP_1$, $CP_2$, $CP_3$, and $CP_4$ at the locations of the remote monitoring units RMU 1 and RMU 2.

A significant (typically several hundred mV) change in pipe-to-soil potential at a particular location will require an investigation of the cause of such a change. For example, the pipe-to-soil potential at a particular test station 40 may historically have been about −1.235V. If a potential of −0.975V is measured during a particular round of monitoring, the change would probably cause the cathodic protection circuits 20 in the vicinity of test station 40 to be checked, looking for electrical shorts to foreign structures or suspecting severe coating damage in the vicinity of test station 40. By placing an RMU at test station 40, this change in pipe-to-soil potential is observed at a central location and the cause for this change may be predicted from the known influence of specific occurrences, such as a 25% voltage difference, without the need for a visit to any of the cathodic protection circuits 20 or to any of the test stations 40.

Referring again to FIG. 6, in accordance with the present invention, by placing a remote monitoring unit at a strategic position, it is therefore possible to "see" a cathodic protection circuit 20 switching off at the remote monitoring unit remote from the cathodic protection circuit 20, because the pipe-to-soil potential at the remote monitoring unit will become more positive as soon as the cathodic protection circuit 20 is switched off. The location of the remote monitoring unit is then made at a location where the influences of the different influencing cathodic protection circuits 20 us distinct and discernable as shown from the placement of the remote monitoring units RMU 1 and RMU 2 in FIG. 6, where there is a substantial difference in pipe-to-soil potential between the influencing rectifiers in $CP_1$, $CP_2$, $CP_3$, and $CP_4$ at the locations of the remote monitoring units RMU 1 and RMU 2.

If the exact influence from each cathodic protection circuit 20 at a particular point is known and if the pipe-to-soil potential at that point is monitored on a regular basis (e.g. daily), it is possible to monitor the cathodic protection circuit 20 without placing the remote monitoring unit at the site of the cathodic protection circuit 20. Because the exact influence from each cathodic protection circuit 20 is known, it is therefore possible to predict when a specific cathodic protection circuit 20 goes out of operation. This concept is illustrated schematically in FIG. 6.

Referring now to FIG. 2 and FIG. 6, the following Table illustrates an example. If RMU1 is positioned at milepost 30 and RMU2 is positioned at milepost 92 and any of rectifiers 20*a,b,c,d* switch off, the pipe-to-soil potential values at RMU1 and RMU2 will change as shown in Table 1.

TABLE 1

| Rectifier Switching Off | Change at RMU1 (mV) | Change at RMU2 (mV) |
|---|---|---|
| 1 | 800 | 0 |
| 2 | 240 | 80 |
| 3 | 50 | 250 |
| 4 | 0 | 420 |

It is clear from the table that RMU1 and RMU2 are positioned in such a way that unique identifiable shifts in pipe-to-soil potential values occur at RMU1 and RMU2. Therefore, the actual cathodic protection circuit 20 going out of operation can be predicted with a high degree of certainty.

The voltage influence curves in FIG. 6 represent the effect of each of rectifiers 24*a,b,c,d* switching off. Sometimes, certain fault conditions cause a decrease in the current output of a rectifier 24 rather than it switching off completely. It should be appreciated that a similar curve can be generated for a decrease of say 25% in the current output of rectifiers 24*a,b,c,d* also. By generating influence curves for a 25% decrease in current output as well as for any of rectifiers 24 switching off completely, it will therefore be possible to "see" a 25% change in current output of any particular rectifier 24 as well as any particular rectifier 24 switching off completely.

In the same way as the influence of rectifiers 24*a,b,c,d* on the pipe-to-soil potential is determined and graphed, the influence of each of rectifiers 24*a,b,c,d* on the pipeline current can be measured at test stations 40 and the results can be graphed as current influence curves. A table similar to Table 1 can be prepared for the influence of each cathodic protection circuit 20 on the current passing through the pipeline at the location of each of the remote monitoring units RMU 1 and RMU 2 of FIG. 6. By incorporating a pipeline current measurement unit 50 instead of a pipe-to-soil measurement unit 42 into remote monitoring unit 62, unique identifiable changes in pipeline current values when a rectifier goes out of service can be measured at RMU1 and RMU2. Therefore, the actual cathodic protection circuit 20 going out of operation can be predicted with a high degree of certainty.

In a preferred embodiment of the present invention, both a pipe-to-soil measurement unit 42 and a pipeline current measurement unit 50 are incorporated into remote monitoring unit 62. By measuring both pipe-to-soil potential and pipeline current at RMU1 and RMU2 in the example in FIG. 6, the certainty of predicting when and which cathodic protection circuit 20 has failed is enhanced significantly.

This monitoring method has a number of benefits associated with it including measuring return current flowing in the pipeline 10 as well as other properties of the pipeline 10. The return current flowing in the pipeline 10 is an important parameter. The current flow back to a rectifier 24 in pipeline 10 at any particular point is determined by the total amount of current picked up by the pipeline 10 before that point. Pipeline current measuring units are used on pipelines for specific troubleshooting and diagnostic purposes. By including a pipeline current measuring unit 50 at an RMU location, the certainty of predicting which cathodic protection circuit 20 has failed is increased because each cathodic protection circuit switching off will cause a unique change in pipeline current at an RMU location.

Sometimes line current measurement units 50 are installed on either side of a pipeline segment, say 1 mile apart. The difference between the return current measured at each line current measurement unit 50 is then equal to the total amount of current picked up by that 1 mile segment of pipeline 10. An increase in the total amount of current picked up by the pipeline segment may be indicative of coating degradation or some other CP upset condition such as a short, and an investigation into the cause of the increased amount of current picked up may be initiated. To date, these measurements are carried out manually by actually visiting test station 40 and measuring the line current using line current measurement unit 50.

As described above, it is preferred not to place remote monitoring units directly at a CP location so that it is possible for one remote monitoring unit to monitor a plurality of cathodic protection circuits 20. It is preferable that the remote monitoring unit be some distance away from each cathodic protection circuit 20, so that the remote monitoring unit can determine whether each one of the plurality of cathodic protection circuits 20 is on and operating. Further, the remote monitoring unit can determine whether a particular cathodic protection circuit 20 is maintaining a certain pipe-to-soil potential.

Another advantage is the flexibility in the placement of the remote monitoring unit. As can be seen from FIG. 6, RMU1 can monitor CPSs 20*a,b,c* while RMU2 may monitor CPSs 20*b,c,d*. Therefore, each of the remote monitoring units is strategically located so that they can discern current pipeline influences from two or more cathodic protection circuits 20. Typically in the prior art, a remote monitoring unit is required for each cathodic protection circuit. However, because the remote monitoring units of the present invention may be strategically located, the number of remote monitoring units may be reduced as compared to the prior art. Further, the reduced number of monitoring units can also monitor and measure the current influences of a plurality of cathodic protection circuits 20 as compared to only one prior art cathodic protection circuit. The pipe-to-soil potential at any particular test station may also be influenced by foreign CPs, i.e. rectifiers belonging to and protecting a pipeline belonging to a second company. A further benefit is therefore that it will also be possible under certain circumstances to monitor the effective operation of multiple cathodic protection circuits belonging to different companies.

An inherent benefit of placing a remote monitoring unit away from the cathodic protection circuit 20 is that the entire section of pipeline 10 between the cathodic protection circuits 20 and the remote monitoring unit can be monitored;

large upsets in the CP status, other than a cathodic protection circuit 20 going out of operation, are detectable at the remote monitoring unit. For example, an uncoated water line may cross the pipeline 10 and electrical shorts to this foreign line may occur. The electrical shorts may be a significant drain on the available CP current and could manifest as a change in pipe-to-soil at the remote monitoring unit, initiating an investigation. In conventional prior art monitoring units, an RMU at the cathodic protection circuit would not detect this change because of the proximity to the current source, or groundbed, and the condition would only be detected during the annual test station survey. In embodiments when a pipeline current measuring unit 50 is part of the remote monitoring unit, the certainty of detecting and predicting specific upsets is significantly increased.

As described earlier, a remote monitoring unit measures pipe-to-soil potential, but may optionally measure other parameters as well, such as pipeline current. When installed at a rectifier to monitor the proper operation of the rectifier, the voltage and current output of the rectifier may be measured. Additional parameters hereinafter described may also be monitored by an RMU.

Figure 7:
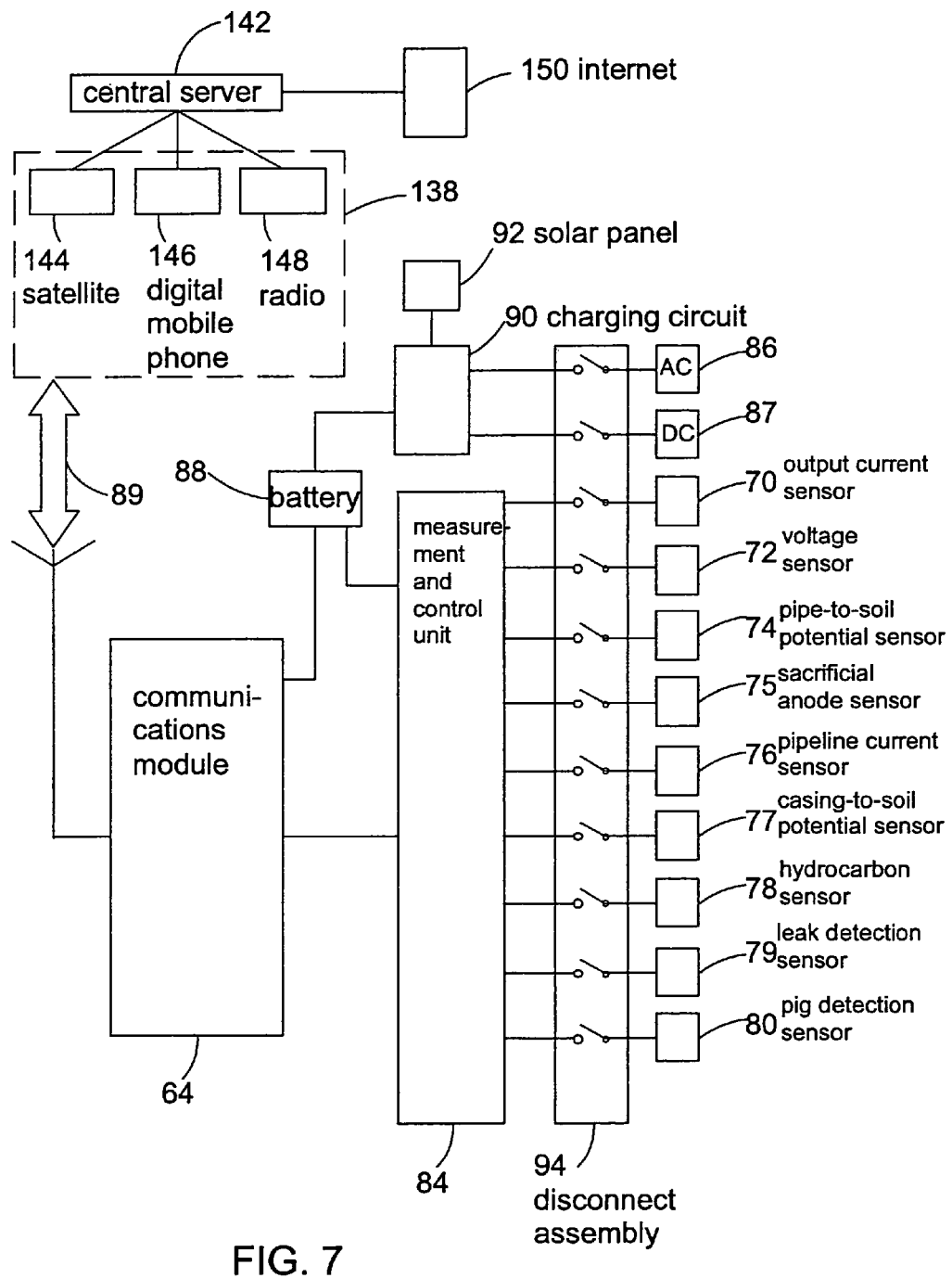
FIG. 7 is a schematic of a remote monitoring unit configuration.

Referring now to FIG. 7, there is shown a schematic of an RMU configuration suitable for monitoring a number of sensors 70 to 80. Sensors 70–80 preferably include an output current sensor 70, a voltage sensor 72, a pipe-to-soil potential sensor 74, a sacrificial anode sensor 75, a pipeline current sensor 76, a casing-to-soil potential sensor 77, a hydrocarbon sensor 78, a leak detection sensor 79, and a pig detection sensor 80. The actual measurement is carried out by measurement and control unit 84, which typically contains volt meters, current meters or other methods of sensing the output from sensors 70 to 80. Measurement and control unit 84 is preferably interfaced to communications module 64 through any one of or a combination of analog to digital or serial interfaces. Measurement and control unit 84 and communications module 64 may also be one integral unit.

A remote monitoring unit may be installed at sites where AC power 86 may or may not be available. At sites where AC power 86 is available, an RMU can be powered directly from the AC power 86, or a battery 88 can provide power and the AC power can be routed through a charging circuit 90 to recharge battery 88. Battery 88 therefore provides back-up power in case of an AC power failure.

If no AC power is available, an RMU can be powered with a long life battery with sufficient capacity that an RMU can operate for a number of years before replacing battery 88, or a solar panel 92 can be used to recharge battery 88. Because communication module 64 typically uses the most power, battery 88 and solar panel 92 are sized to provide sufficient power for the required data transmission frequency. The battery 88 may be a lead-acid, nickel-cadmium, nickel metal hydride or any other battery that may be charged by solar panel 92 or AC power 86. The circuitry for a remote monitoring unit will normally be in the sleep mode or off mode and will only switch on when measurements are taken (typically once per day) thus preserving power and allowing battery 88 to be recharged. Alternatively, the remote monitoring unit may be kept in a standby mode allowing communications at any time, provided sufficient recharging of battery 88 occurs through solar panel 92.

As discussed above, remote monitoring units are prone to damage by electrical surges, which are the most common cause for failure. Surges may enter the unit through the AC supply, through the hardwire connections to the pipeline 10 or rectifier 24 or through connections to other sensing devices 70 to 80. Electronic surge protection devices (e.g. MOV, spark gap etc.) are currently used but are not totally effective, and either do not block all the surges or eventually fail. Because lightening causes kilovolt surges in a pipeline, a simple relay may allow the electricity to arc across the contacts of the relay. Thus, there must be a large dielectric strength between contact points. This can be achieved by placing a substantial distance between the two contact points. Statistically, the chance of a lightening strike during the period of operation of the present invention unit is very remote. Disconnect assembly 94 in FIG. 7 provides the required dielectric strength between contact points.

Figure 8:
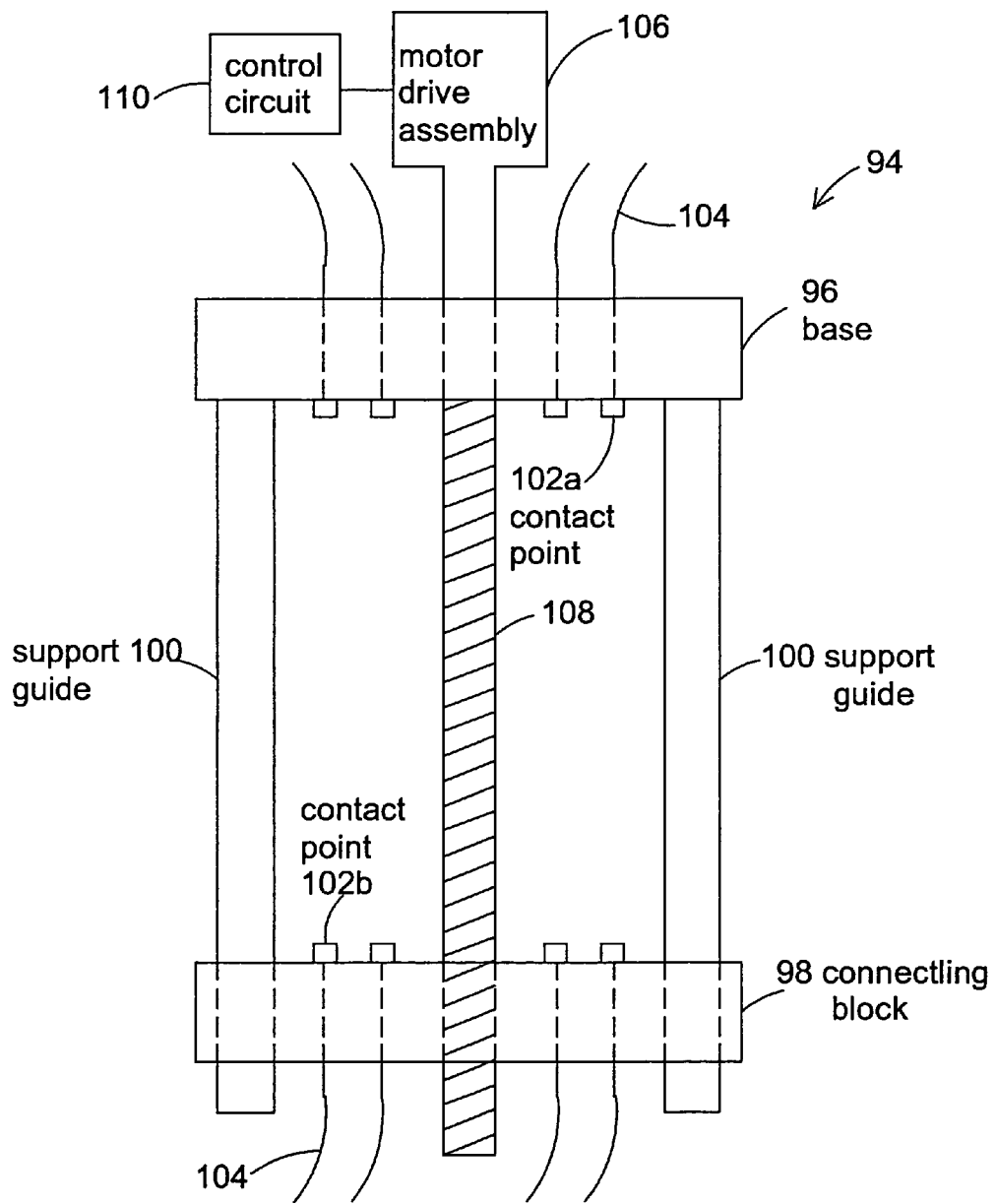
FIG. 8 is a schematic of a disconnect device for use in a preferred embodiment of the present invention.

Disconnect assembly 94, shown in detail in FIG. 8, is a preferred embodiment of the present invention. In this embodiment, disconnect assembly 94 includes a stationary base 96 and a moving connecting block 98. Support guides 100 are connected to base 96 and connecting block 98 slides over support guides 100 toward and away from base 96. Base 96 is preferably fitted with contact points 102a and connecting block 98 is preferably fitted with contact points 102b. Contact points 102a,b may be spring loaded and may be plated with an inert metal to prevent oxidation. Insulated electrical conductors 104 are connected to contact points 102a,b and provide a means for electrical connection. Connecting block 98 is moved into an open or closed position with a motor drive assembly 106, which turns a threaded shaft 108. Threaded shaft 108 preferably screws through connecting block 98 and moves freely in base 96. Therefore, when motor drive assembly 106 rotates in one direction, connecting block 98 moves towards base 96 into the closed position, and when the motor drive assembly 106 rotates in the other direction, connecting block 98 moves away from base 96 into the open position. Motor drive assembly 106 may comprise any motor configuration, such as a DC motor with a gear drive capable of rotating threaded shaft 108 in either direction to provide an air gap between the contact points when connecting block 98 and base 96 are in the open position. One preferred air gap is at least 1 inch and preferably 2 inches. In addition, disconnect assembly 94 may include limiting switches (not shown), which determine the open and closed position for connecting block 98. This design therefore allows for controlling the distance that connecting block 98 moves away from base 96 in the open position.

Disconnect assembly 94 may optionally include a control circuit 110, allowing control and monitoring of disconnect assembly 94 using digital input and output capabilities of measurement and control unit 84 or communication module 64. In some embodiments, measurement and control unit 84 or communication module 64 include a timer that activates the disconnect assembly 94 at a predetermined frequency (e.g. once a day) to perform measurements and tests. The disconnect assembly 94 is moved to the closed position for taking a measurement or test and then moved to the open position after the measurement or test has been taken. Furthermore, control circuit 110 may include a microprocessor (not shown) with on-board clock allowing programming of disconnect assembly 94. Control circuit 110 with the microprocessor makes it possible to program disconnect assembly 94 to open and close at pre-set times without the need for other external control signals. In addition, control circuit 110 with the microprocessor can provide feedback on the status of disconnect assembly 94 such as confirmation that disconnect assembly 94 is in the open or closed position.

In one embodiment, the disconnect assembly 94 is a multiple contact device; four contacts are shown in FIG. 8.

Disconnect assembly 94 is not limited to 4 contacts and more or less than 4 contacts may be required in certain measurement configurations.

Since disconnect assembly 94 is only connected a few seconds or minutes a day, it is therefore disconnected most of the time. As a result, there is no need for an electrical storm detector. Secondly, the substantial separation distance between contact points 102a and contact points 102b eliminates the need for a dielectric between the contact points 102a and 102b. Thus, there is a predetermined air gap in the open position such that arcing across the gap cannot occur.

An advantage of the present invention is that the circuits in the remote monitoring unit do not have to be in the on or active state at all times, but only need to switch on when a measurement is to be carried out. It is therefore possible to isolate all inputs to the circuits during times when no measurements are carried out and only to switch the circuits on for the few minutes per day when measurements are carried out and data transmitted. The remote monitoring unit need only be on for seconds/minutes a day rather than 24 hours a day as in the prior art. All measurements can be acquired within seconds/minutes, typically less than 5 minutes. Thus, there is no reason to keep hard wire connections between the remote monitoring unit and pipeline 10 and between the remote monitoring unit and sensors 70 to 80 throughout the day. Referring back to FIG. 7, other circuits such as the AC or DC power supply or an antenna 89 of a communications system 138 may also be disconnected if required. There is no need for a permanent connection. In a preferred embodiment, all circuits are disconnected at all times when measurements are not being taken.

It should be appreciated that while the present invention has been described using disconnect assembly 94, other disconnect assemblies may be used, provided the disconnect assembly is in the off state most of the time. Such other disconnect assemblies may be alternative designs where an air gap is created of at least 1 to 2 inches between contact points, or it may also be some other form of switch, e.g. a relay. Provided the disconnect assembly is in the off position most of the time, the level of protection offered by any particular design will vary depending on the dielectric strength between the contact points in the open position. A typical electrical relay may only provide protection up to a 2 kV surge whereas disconnect assembly 94 may provide protection up to several hundred kV if the contact points are several inches apart in the open position.

It should also be appreciated that a disconnect assembly can also be used to prevent damage from surges when the RMU is installed at the rectifier site and the RMU not only measures the pipe-to-soil potential 74 or pipeline current 76 but also the output current 70 and voltage 72 of the rectifier. By routing all connections to pipeline 10 or ground bed 30 through disconnect device 94 and by keeping disconnect device 94 open during times when the RMU is in a standby mode and actual measurements are not being carried out, the possibility of damage to the RMU by surges from the pipeline, the ground bed or other sensors 70 to 80 is significantly reduced.

When an RMU is installed at a rectifier, AC power is typically available and it is therefore convenient to power the RMU from this AC source. This permanent connection to the AC power is a possible source of surges which could damage the RMU. However, disconnect device 94 combined with back-up battery 88 provides a unique means for protecting the RMU from damage by electrical surges through the AC circuit 86 while still maintaining the benefit of the convenient AC power through the AC circuit 86. The control of disconnect device 94 afforded by control circuit 110 or by measurement and control circuit 84 or by communication module 64, provides a means of keeping the AC power disconnected most of the time (preferably at least 80% of the time) during which time battery 88 remains sufficiently charged to operate the RMU. In this application, the AC supply will be connected to the remote monitoring device and/or to other associated devices through disconnect assemblies 94. When disconnect assembly 94 closes to make a measurement, the AC power is connected, allowing battery 88 to be recharged. In addition, the RMU or associated electronic devices senses the battery 88 voltage continuously, so that when the battery 88 voltage drops below a pre-set value, disconnect assembly 94 automatically closes. This connects the AC supply 86 allowing recharging of battery 88. The possibility of damage to the remote monitoring device or other associated electronic equipment by surges on the AC circuit is therefore limited to the time that measurements are taken or to the time that recharging of battery 88 occurs.

The level of surge protection provided to the RMU at a site where AC power is available may be increased even further by using both AC power 86 and solar panel 92 to recharge battery 88. By connecting solar panel 92 permanently to battery 88, most of or all of the power required to recharge battery 88 is provided by solar panel 92. Connection to AC power 86 through disconnect device 94 is now only required when the power supplied by solar panel 92 is exceeded. The total time that the RMU is connected to AC power and therefore the total time that the RMU is exposed to surges on the AC circuit has therefore been reduced even further by incorporating solar panel 92.

It should further be appreciated that disconnect assembly 94 can be used to protect any device from electrical surges where the device only needs to be connected to the source of the surge for short periods of time. Furthermore, disconnect assembly 94 can be used in other applications which are otherwise prone to damage by electrical arcing across contact points.

Figure 9A:
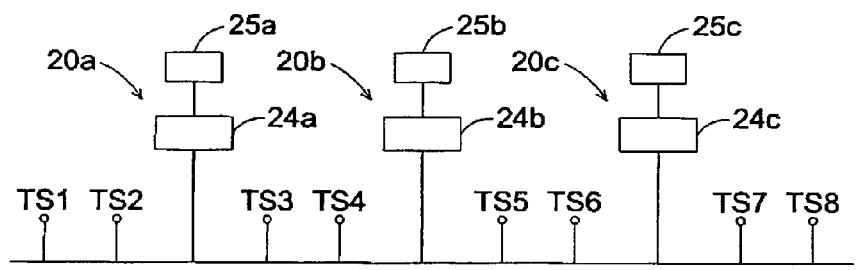
FIG. 9A is a schematic of a cathodic protection system with interrupters at the rectifiers.

Referring now to FIG. 9A, there is shown a typical CP configuration like that of FIG. 2. The example CP configuration includes three cathodic protection circuits 20a,b,c with rectifiers 24a,b,c and 8 test stations 40, TS1 to TS8.

To determine the "interrupted off" or "instant off" pipe-to-soil potential of the three cathodic protection circuits 20a,b,c with rectifiers 24a,b,c, the pipe-to-soil potential is measured at each of the test stations 40, TS1 to TS8, within approximately 1 second after all of the rectifiers 24a,b,c have been turned off in unison. To determine the "on" pipe-to-soil potential of the three cathodic protection circuits 20a,b,c with rectifiers 24a,b,c, the pipe-to-soil potential is measured at each of the test stations 40, TS1 to TS8, while all of the rectifiers 24a,b,c are turned on. This measurement procedure is achieved by installing current interrupters 25a, b,c into each influencing rectifier 24a,b,c and programming these interrupters 25a, 25b, and 25c to switch off and on at the same time so as to allow pipe-to-soil measurements to be taken during the "off" and "on" intervals. Synchronization of the various interrupters is achieved through synchronizing their internal clocks, often using satellite time signals. It is also typical for such interrupters to have a common known reference point, or point of zero time. This ensures that if any one interrupter within a group of operating interrupters is arbitrarily turned off and on again during an interruption cycle, that particular interrupter will actually resume its interruption cycle in unison with any other interrupters already operating. Typically, the top of the hour or the top of the day are used as the common known reference point, and when an interruption cycle is initiated, the interrupter calculates at which point in time it needs to initiate a particular interruption cycle so that it switches on and off in unison with any other interrupters operating at the same interruption cycle. U.S. Pat. No. 4,356,444, hereby incorporated herein by reference, describes a plurality of interrupters which switch rectifiers on and off in unison. Each interrupter is synchronized with a clock reference unit.

Figure 9B:
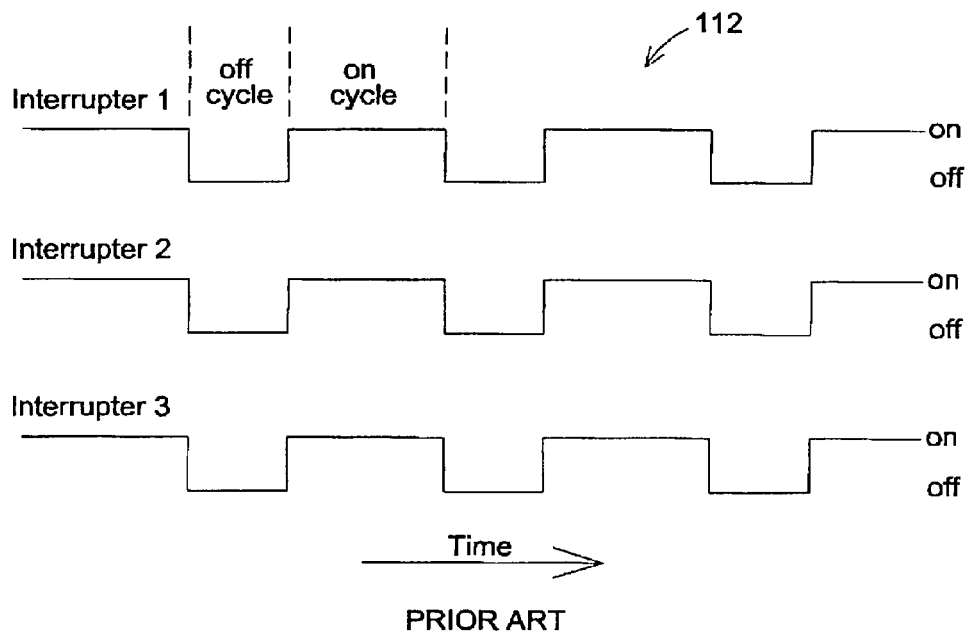
FIG. 9B is a chart of the on and off cycles of the interrupters of FIG. 9A when the interrupters are synchronized.

FIG. 9B shows the typical prior art "on" and "off" cycles that are generated for three interrupters that are presently commercially available. Some of the available interrupters only have fixed "on" and "off" cycles while others are programmable and the length of the "off" and of the "on" cycle can be adjusted. Some models have the ability to also program the start and stop time for the interruption cycle. In all the equipment currently available, all the interrupters switch on and off at the same time.

In the prior art, in order to evaluate the pipe-to-soil influence from each rectifier 24 in this example, it is necessary to switch each of the rectifiers 24 off, while the remaining rectifiers are left on, and measure the pipe-to-soil potential at each test station 40. For example, a rectifier 24 is switched off, while the remaining rectifiers are left on, and the pipe-to-soil potential is measured at a test station 40. The rectifier 24 is then turned back on and the pipe-to-soil potential is measured again at the test station 40. The shift of the pipe-to-soil potential from off to on at each test station can then be determined.

Instead of manually switching each rectifier 24 off and on, it is common in the CP industry to install a current interrupter 25 into the rectifier 24 under investigation. A current interrupter is a device that interrupts the output from the rectifier 24 in a periodic fashion and is typically programmable so that the length of the on and off cycles can be adjusted. By installing an interrupter 25 into a rectifier 24, such as 24a, it is therefore possible to visit test stations TS1 to TS8 and measure the influence of rectifier 24a being interrupted. The influence of rectifiers 24b,c is then measured by moving the interrupter 25 to each of these rectifiers in turn and re-visiting test stations TS1 to TS8.

In the prior art, to determine rectifier influence at each test station in FIG. 9A, an interrupter must be moved from rectifier to rectifier and each of the test stations TS1 to TS8 visited for pipe-to-soil potential measurements a total of three times. If the "instant off" value needs to be measured at test station TS1 to TS8 also, it is necessary to install interrupters 25a,b,c into all three rectifiers 24a,b,c. Interrupters 25a,b,c are programmed to produce a unison switching cycle 112 described in FIG. 9B which causes each of rectifiers 24a,b,c to switch "on" and "off" in unison. A fourth visit to each of test stations TS1 to TS8 is required to measure the "instant off" value during the "off" cycle. Currently no device is available that will allow measurement of the influence from each rectifier and the "instant off" pipe-to-soil potential without the multiple visits to test stations and rectifiers described above.

The apparatus and methods of the present invention include a system which can be programmed to obtain the rectifier influence, the "on" potential, and/or the "instant off" potential at each test station 40 during a single visit to each test station 40. This system furthermore has the capability of providing a switching cycle on a plurality of influencing rectifiers 24 allowing the simultaneous measurement of rectifier influence, "on" potential, and "instant off" values at test stations 40, all collected during a single visit to the test stations 40. At present, there is also no way of obtaining the rectifier influence in conjunction with "on" potential, and "instant off" potential values in a single visit to the test stations 40 because the rectifiers 24 are either "on" or "off" as shown in FIG. 9B.

Figure 9C:
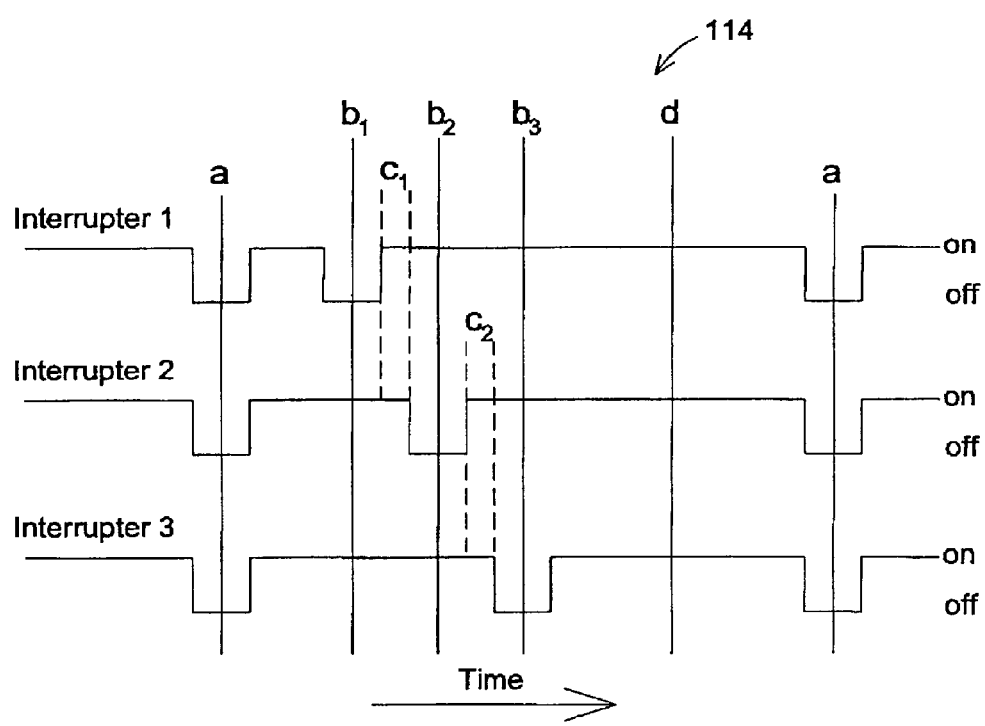
FIG. 9C is a chart of the on and off cycles of the interrupters of FIG. 9A when the interrupter time cycles are staggered.

Referring now to FIG. 9C, there is shown a preferred method of the present invention. Considering the CP configuration described in FIG. 9A, three current interrupters 25a, 25b, 25c can be programmed to produce a consecutive switching cycle 114. Consecutive switching cycle 114 will allow the measurement of the influence of each of the three rectifiers 24a,b,c as well as the "instant off" and "on" pipe-to-soil potential during a single visit to each of test stations TS1 to TS8. The time periods, labeled "a" through "d", for the "off" and "on" settings for the three interrupters 25a, 25b, 25c are as follows:

(a) During time period (a), all rectifiers 24 shown in FIG. 9A are switched off to record the "instant off" potential.

(b1) During time period (b1), rectifiers 24b,c are on and rectifier 24a is off and the influence from rectifier 24a is recorded.

(c1) During time period (c1), all rectifiers 24 are on to provide a stabilization time between time periods (b1) and (b2).

(b2) During time period (b2), rectifiers 24a,c are on and rectifier 24b is off and the influence from rectifier 24b is recorded.

(c2) During time period (c2), all rectifiers 24 are on to provide a stabilization time between time periods (b2) and (b3).

(b3) During time period (b3), rectifiers 24a,b are on and rectifier 24c is off and the influence from rectifier 24c is recorded.

(d) During time period (d), all rectifiers 24 are on. Time period (d) is typically of sufficient duration to allow the "on" pipe-to-soil voltage potential to be measured. It should be noted that the "on" potential can also be measured during time period (c), provided time period (c) is of sufficient duration to carry out this measurement.

The difference between the pipe-to-soil potential measurements during time period (d) and during time periods (b1), (b2) and (b3) will therefore provide the influence (in mV) of rectifiers 24a,b,c while the pipe-to-soil potential measured during time period (a) provides the "instant off" potential. The pipe-to-soil potential measured during time period (d) provides the "on" potential. The need for multiple visits to the same test station in the prior art has therefore been eliminated.

Using the switching cycle described above, it is also possible to measure the change in current flow back to each rectifier 24 in pipeline 10 at each test station 40 caused by switching each rectifier 24 off. This change in current flow at every test station 40 may be measured using the configuration described in FIG. 4 or it can also be measured by alternative means such as by measuring the change in the magnetic field around pipeline 10 caused by the change in current flow.

In addition to measuring the pipe-to-soil potential at each test station, it is sometimes also necessary to measure the pipe-to-soil potential between test stations 40 at a regular distance interval. This measurement procedure is typically referred to as a close interval survey (CIS). A CIS is routinely performed in the pipeline industry and is typically performed on a pipeline where the pipe-to-soil potential data collected at test stations (typically spaced 1 mile apart) alone is deemed inadequate and a higher density of data points is required. The spacing of data collection points on a CIS varies, but 2.5 to 5 foot intervals are typical. In the prior art, a CIS is typically performed while switching all influencing rectifiers 24 on and off in unison as shown in FIG. 9B so that the "on" potential and also the "instant off" potential can be recorded at regular measurement intervals.

Figure 9D:
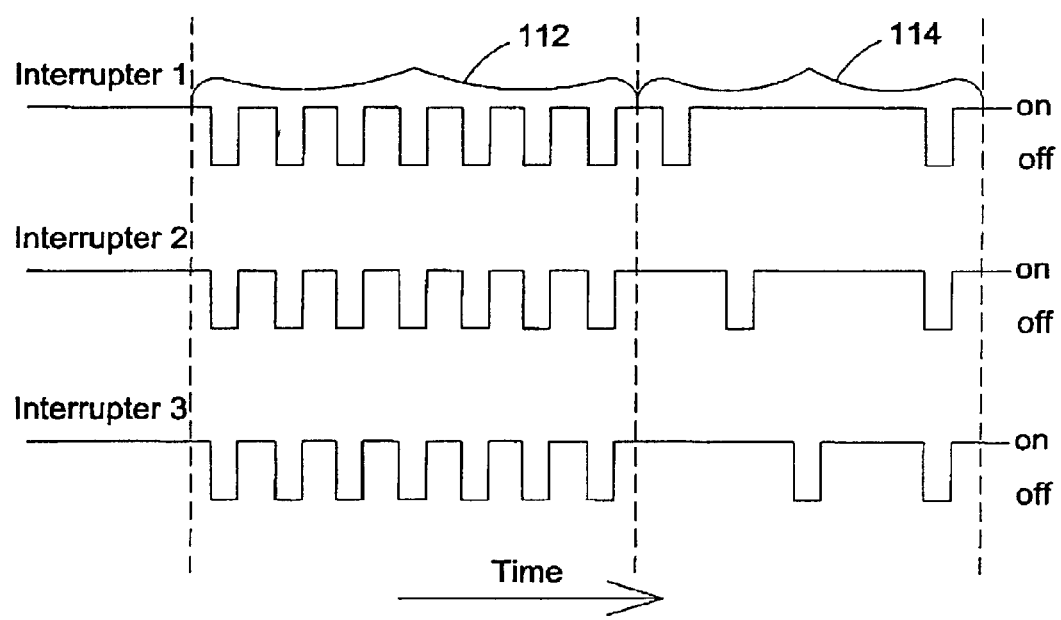
FIG. 9D is a chart combining the time cycles shown in FIG. 9B and FIG. 9C.

Referring now to FIGS. 9A, 9B, 9C and 9D, the switching of rectifiers in unison described in FIG. 9B and the consecutive switching of rectifiers shown in FIG. 9C can be combined to produce the time cycle described in FIG. 9D. By using the time cycle described in FIG. 9D, it is now possible to perform a CIS between TS1 and TS8 and to measure the "on" and the "instant off" potentials at regular distance intervals during unison switching cycle 112 in FIG. 9D and then to also measure the influence from each rectifier being interrupted during consecutive switching cycle 114 in FIG. 9D. After completion of at least one consecutive switching cycle 114, unison switching cycle 112 is preferably repeated and so on.

In a preferred embodiment of this invention, the duration of unison switching cycle 112 is programmable so that the amount of "on" and "instant off" data that is collected during unison switching cycle 112 can be adjusted. For example, when conducting a CIS survey using the combined cycle described in FIG. 9D, unison switching cycle 112 can be programmed to be 5 minutes. The resulting switching cycle will then consist of 5 minutes of regular "on" and "off" switching followed by consecutive switching cycle 114. In practice, the CIS surveyor will therefore manually progress along the pipeline 10 for 5 minutes, as in a normal CIS, taking "on" and "instant off" readings at the appropriate distance interval, typically every 2.5 feet. The surveyor is then alerted when consecutive switching cycle 114 is about to occur (audibly and/or visually) and the surveyor then remains stationary with the reference electrode 46 contacting the ground 48 until consecutive switching cycle 114 is completed. For the next five minutes unison switching cycle 112 occurs and the surveyor continues walking, taking "on" and "instant off" readings at regular intervals until the next consecutive switching cycle 114 is about to occur, and so on. In this example, the influence from rectifiers 24a,b,c will therefore be measured at various points along the pipeline 10 at 5-minute intervals. The distance between the locations where the influence from rectifiers 24a,b,c is recorded will vary according to the rate at which the surveyor walks along the pipeline 10 and also by the programmed duration of unison switching cycle 112.

The methods described above is not limited to 3 rectifiers, but can be expanded to any number of rectifiers. A sufficient number of rectifiers can therefore be interrupted so that a survey can be carried out for at least one day without moving into the influence area of an uninterrupted rectifier. Due to the fact that the internal clocks of all interrupters are accurately synchronized and that the actual times during which the time periods (a) to (d) occur are known, it is also possible to relocate interrupters during a survey without reprogramming all the interrupters, provided the surveyor knows the location of each interrupter. For instance, interrupter 25a in FIG. 9A can be moved from rectifier 24a to a fourth rectifier (not shown) without reprogramming any of the interrupters.

It is possible to read the pipe-to-soil values manually while carrying out the interruption cycles shown in FIGS. 9C and 9D but it is preferable to use a data logger. By synchronizing the internal clock of the logger with the internal clocks of the interrupters, for instance through a global positioning system interface, the logger can be programmed to record pipe-to-soil potential values during the appropriate time within the interruption cycles shown in FIG. 9C or 9D. Referring again to FIG. 9C, the logger is programmed to read, display and store the "on", "instant off", "influence from rectifier 24a", "influence from rectifier 24b" and "influence from rectifier 24c" values automatically. Referring again to FIG. 9D, the logger is also programmed to read, display and store each of the "on" and "instant off" values for the duration of time period (b) and to then read, display and store the "influence from rectifier 24a", "influence from rectifier 24b" and "influence from rectifier 24c". Because the internal clock of the logger is synchronized with the interrupters, the logger can also be programmed to alert the surveyor when unison switching cycle 112 has elapsed.

A system has therefore been described that allows the measurement of CP influence in conjunction with routine CP measurements without substantially increasing the time or effort required. The CP influence results can then be used to position RMUs along the pipeline. It should be noted that use of this system is not limited to studying the influence from rectifiers installed on pipeline 10, but it includes studying the influence from foreign rectifiers, i.e. rectifiers supplying current to other pipelines in the vicinity which may influence the potential profile on pipeline 10. This information is also important for placement of RMUs and it also assists in evaluating possible detrimental influences from foreign rectifiers. Normally, a separate study is carried out to assess the possible detrimental influence from foreign rectifiers. Additionally, this information allows the surveyor to create a more detailed influence curve, exemplified in FIG. 6, because more data points are known.

Because the detailed rectifier influence data greatly increases the flexibility of positioning a remote monitoring unit along pipeline 10, additional parameters, other than just pipe-to-soil potential and/or pipeline current may be measured on the pipeline 10. The placement of a remote monitoring unit for these additional parameters alone may not have been economically viable, but combined with the pipe-to-soil potential and rectifier status monitoring, measurement of these additional parameters add significant value. In essence, the placement of the remote monitoring units may be determined by the cathodic protection circuit influence alone, or in combination with other influences, described below, when there is a need for additional monitoring at specific points on the pipeline 10.

Figure 10:
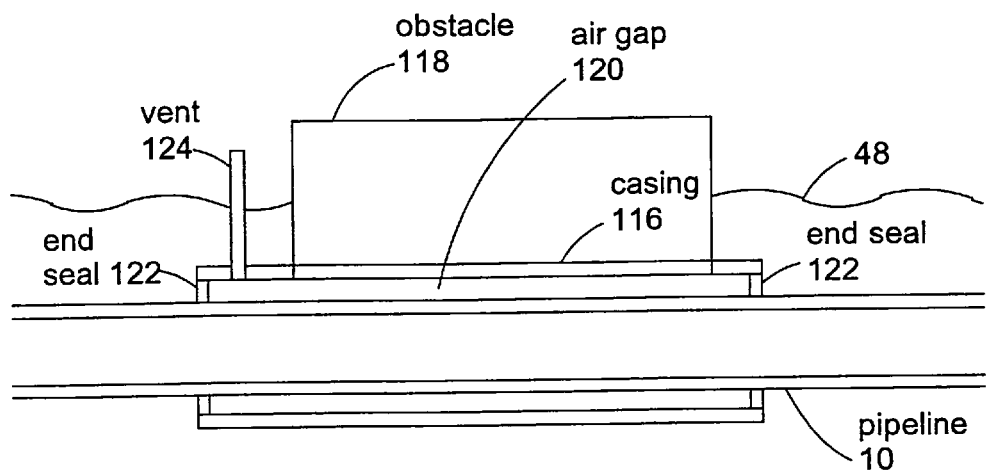
FIG. 10 is a schematic of a preferred embodiment of the present invention for measuring the pipe-to-soil potential of a casing that surrounds the pipeline.

Referring now to FIG. 10, the method and apparatus of the present invention may also be used to measure the pipe-to-soil potential of a casing 116 that surrounds the pipeline 10. Often, when a pipeline 10 passes underneath a roadway, railway, or other obstacle 118, a casing 116 is placed around the pipeline 10. Typically the casing 116 around the pipeline 10 includes an air gap 120. The casing 116 has end seals 122 between the end of the casing 116 and the pipeline 10 to keep water from passing into the air gap 120. If the air gap 120 fills up with electrolytes, such as water, there is a possibility that corrosion can occur. It is also important that there is no metal contact between the casing 116 and the pipeline 10. Thus, it is important to monitor the pipe-to-soil potential of the casing 116 since it will be different from the pipe-to-soil potential of the pipeline 10. As their potentials become similar in value, this is an indication of either a metallic short between the casing 116 and pipeline 10 or an indication that electrolytes have entered the air gap 120.

The method and apparatus of the present invention may also be used to monitor the hydrocarbons in the casing 116. The casing 116 has a vent 124 that extends from the air gap 120 between the casing 116 and pipeline 10 to above ground 48 such that a transducer (not shown) may be placed at the vent 124 to detect whatever hydrocarbons are released by the pipeline 10. If there is a leak in the casing 116, the leak will be detected.

Figure 11:
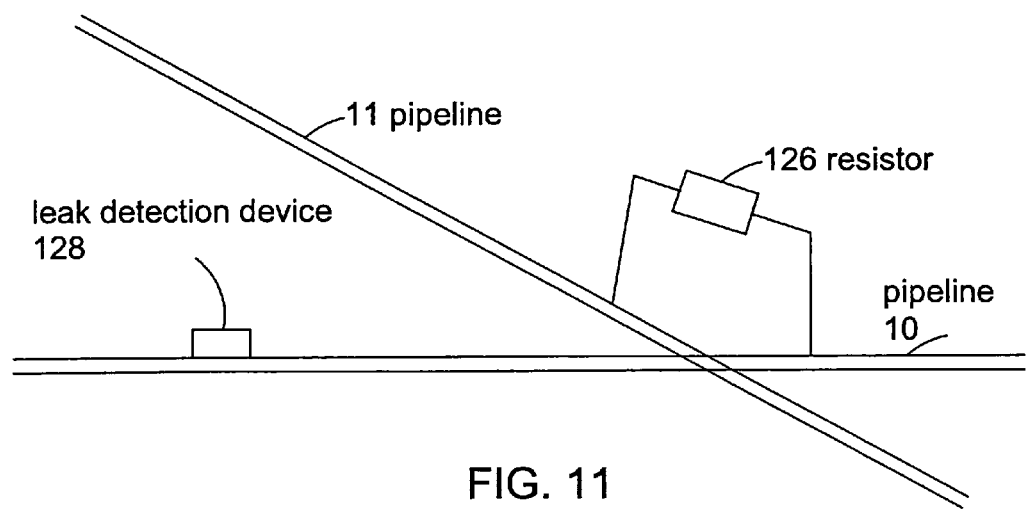
FIG. 11 is a schematic of a preferred embodiment of the present invention for monitoring a bond between two pipelines.

Referring now to FIG. 11, there is shown the method and apparatus of the present invention being used to monitor a bond between two pipelines 10, 11. For example, referring back to FIG. 6, RMU2 may be placed at milepost 93 instead of milepost 92 because of a critical bond to a foreign pipeline at milepost 93. It then becomes possible to monitor the integrity of this bond in addition to monitoring the status of the cathodic protection circuits 20. A resistor 126 is placed between the two pipelines 10, 11 to control the amount of current flow and/or to determine how much current is actually passing between the two pipelines 10, 11.

There are also various leak detection devices 128 that may be attached and buried with the pipeline 10. Such detection devices 128 may also be monitored and measured.

Figure 12:
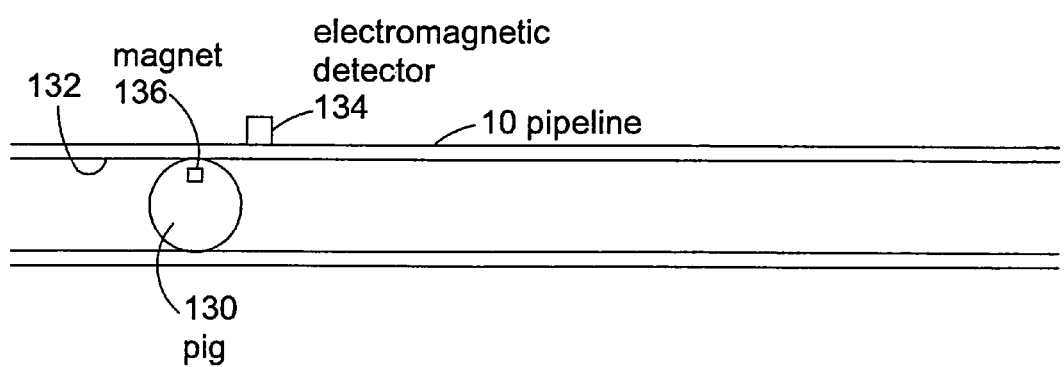
FIG. 12 is a schematic of a preferred embodiment of the present invention for monitoring pigs passing through the pipeline.

Referring now to FIG. 12, the method and apparatus of the present invention may be used to detect the passage of pigs 130 through the pipeline 10. Pigs 130 are passed through the pipeline 10 to clean the pipelines and to separate batches of hydrocarbon products. The pig 130 is similar to an elastomeric sphere that is pushed by the product passing through the pipeline 10. The elastomeric sphere 130 scrapes against the inner surface 132 of the pipeline 10 as it passes through the pipeline 10 thereby cleaning the interior walls 132 of the pipeline 10. Some pigs 130 are instrumented to measure and record metal loss, dents and other conditions of the pipeline. The remote monitoring units can monitor and track the progress of the pig 130 as it passes through the pipeline 10 so as to sense if the pig 130 becomes stuck. One type of sensor 134 for sensing a pig 130 is a geophone receiver attached to the pipeline 10 to monitor the noise made by the passing of the pig 130 through the pipeline 10. Other types of sensors 134 are a hydrophone to monitor the noise from the pig 130. Another is an electromagnetic detector 134 mounted on the pipeline 10 to sense a magnet 136 disposed within the pig 130 to detect the pig 130 as it passes through the pipeline 10 beneath the electromagnetic detector 134. The monitoring unit might have to be left on for a substantial period of time to detect the passage of a pig 130.

Referring back to FIG. 7, other parameters that can be monitored in combination with a pipe-to-soil potential 74 include, but are not limited to, casing-to-soil potential 77, pipe current 76, "sniffing" for hydrocarbons 78 in a casing vent 132, detection of a pig's passage 80 past a specific critical point (e.g. a valve), monitoring of leak detection devices 79, and monitoring the output of sacrificial anodes 75. In addition, the location of the remote monitoring unit may be used as an above ground reference point for smart pigging operations.

It is preferable for the analysis of results from various remote monitoring units to be controlled by special custom software and known set points; the influence from each cathodic protection circuit 20 (exemplified in the Table 1) are programmed in. As a result, the pipeline operator can be alerted of any upset conditions and the software can predict the nature of the upset condition.

In a preferred embodiment, the present invention is multifunctional and capable of remotely monitoring many parameters at any specific location. Because the remote monitoring unit location is not limited to a cathodic protection circuit location (as is the case with conventional rectifier remote monitoring), the proposed methodology allows flexibility in terms of the exact location of the remote monitoring unit.

Referring again to FIG. 7, there is shown a schematic of the method and apparatus of the present invention including a communication module 64 and a measurement and control unit 84 receiving power from one or more power sources such as an AC power source 86, DC power source 87 or a solar panel 92. Each of these power sources is routed through a charging circuit 90 which controls recharging of battery 88 as previously described. A disconnect assembly 94 serves as a switch to the sensors 70 to 80 and also to AC power 86 or DC power 87 as previously described.

Communication system 138 is used to relay the data from communication module 64 to a central location. The communication system 138 makes it unnecessary to visit each of the remote monitoring units or each of the rectifiers since by knowing the influence from each of the cathodic protection circuits 20 as measured by the remote monitoring units, the status of cathodic protection circuits 20 can be determined from changes in pipe-to-soil potential measured by the remote monitoring unit.

The communication system 138 communicates with a central server 142 at a remote central location. Such communication may occur using a satellite 144, an analog or digital mobile phone 146, a land line (not shown), or a radio 148 to transmit the data from the communications module 64 to the server 142. Any other form of communication capable of transmitting data over significant distances may be used. The communications module 64 and/or the measurement and control unit 84 preferably include a logger to store the data and measurements taken by measurement and control unit 84. The logger interfaces with the communication system 138. The communications system 138 receives the data from the communication module 64 and then transmits the data remotely to the server 142. The communication system 138 preferably includes antenna 89 that communicates with one of the communicators such as satellite 144, cellular phone 146, or radio 148. U.S. Provisional Patent Applications Ser. Nos. 60/128,513 and 60/129,708 each filed Apr. 7, 1999 and entitled "Remote Data Access and -System Control" and U.S. patent application Ser. No. 09/545,379, filed Apr. 7, 2000, entitled "Remote Data Access and System Control", all hereby incorporated herein by reference, disclose an example communication system.

Once the data has been transmitted back to the server 142, the data is then accessed through the Internet 150. The measurements are collated with a particular time such that a database is produced for each individual cathodic protection circuit 20 as well as the pipeline 10. Each rectifier has its own unique identification such that a communication system 138 receives data from approximately 50 different operating units, the data is collected, and then transmitted to a central station which is then picked up by the server. The server is able to identify each of the data packages associated with each of the remote operating units.

There is two-way communications between the remote monitoring unit and the server 142. The communication back to the monitoring unit may merely be an acknowledgement of the receipt of the transmission of the data. However, it should be appreciated that control functions can also be communicated and performed. For example, the time period within which measurements are to be taken may be altered remotely. Further, with two-way communication, a remote operating unit may be turned off during an electrical disturbance. The system can also include a rain sensor, a light sensor, or a lightening sensor to vary the operation of the remote monitoring unit.

The data is interpreted by the central server 142 and may be graphed showing whether the pipe-to-soil potential or the pipeline current had changed from a baseline value. Software may be used to analyze the data and apply it to the calibration graphs such as FIG. 6. The calibration graph provides base line data for each remote operating unit that is then compared to the data received remotely from each unit over time. The software includes graphs and actually shows the schematic of the pipeline with remote operating units and cathodic protection systems on the pipeline. This data is applied to the base data to detect a variance. It may further determine the significance of any variance. Customers may be able to access the data at the server 142 using the Internet 150.

It should be appreciated that the remote monitoring unit may also be programmed to detect and report a variance from a baseline value. This functionality may be combined with scheduled reporting of the measured value or it may also be used instead of scheduled reporting. The frequency of data transmissions can therefore be further reduced by incorporating the alarm feature described above. As a result, communication costs may be reduced. Furthermore, the total time that disconnect device 94 needs to be in the closed position may be reduced because transmission time is reduced, resulting in extended battery 88 life and a decrease in the possibility of damage by electrical surges.

While the present invention has been disclosed and described in terms of a preferred embodiment, the invention is not limited to the preferred embodiment. For example, while the present invention has been described for use in monitoring pipelines, it should be understood that it could be used in monitoring any structure susceptible to corrosion. In addition, various modifications to the preferred embodiments, among others can be made without departing from the scope of the invention. In the claims that follow, any recitation of steps is not intended as a requirement that the steps be performed sequentially, or that one step be completed before another step is begun, unless explicitly so stated.

What is claimed is:

1. A current interrupter assembly for a pipeline having a plurality of test stations, the assembly comprising:
    a first current interrupter connected to a first cathodic protection circuit having a first rectifier;
    a second current interrupter connected to a second cathodic protection circuit having a second rectifier;
    a third current interrupter connected to a third cathodic protection circuit having a third rectifier;
    each of said current interrupters having internal clocks that are synchronized together;
    said internal clocks of said current interrupters being programmed to produce a consecutive switching cycle;
    said consecutive switching cycle including
        during a time period (a), all of said rectifiers are switched off and an instant off potential is recorded;
        during a time period (b), second and third rectifiers are on and said first rectifier is off and an influence of said first rectifier is recorded;
        during a time period (c), all of said rectifiers are on for a stabilizing time;
        during a time period (d), first and third rectifiers are on and said second rectifier is off and an influence of said second rectifier is recorded;
        during a time period (e), all of said rectifiers are on for a stabilizing time;
        during a time period (f), first and second rectifiers are on and said third rectifier is off and an influence of said third rectifier is recorded; and
        during a time period (g), all rectifiers are on.

2. The current interrupter assembly of claim 1 wherein during either time period (c), (e) or (g), the on pipe-to-soil potential is measured.

3. The current interrupter assembly of claim 1, wherein during the time period that each of said rectifiers is individually switched off, a change in current flow back to the switched off rectifier is measured at each test station.

4. The current interrupter assembly of claim 1, wherein during the time period that each of said rectifiers is individually switched off, a change in the magnetic field around the pipeline is measured at each test station to determine the current flow back to the switched off rectifier.

5. The current interrupter assembly of claim 1, wherein a close interval survey is programmed to be performed to measure the on and off pipe-to-soil potentials between test stations at regular distance intervals.

6. The current interrupter assembly of claim 1, wherein said consecutive switching cycle may be reprogrammed remotely.

* * * * *